US011147149B2

(12) United States Patent
Nishimura et al.

(10) Patent No.: US 11,147,149 B2
(45) Date of Patent: Oct. 12, 2021

(54) X-RAY INSPECTION DEVICE

(71) Applicant: ISHIDA CO., LTD., Kyoto (JP)

(72) Inventors: Hiromu Nishimura, Ritto (JP); Shingo Kondo, Ritto (JP); Kaname Nishiue, Ritto (JP); Shinya Makino, Ritto (JP); Kotaro Kobayashi, Ritto (JP)

(73) Assignee: ISHIDA CO., LTD., Kyoto (JP)

( * ) Notice: Subject to any disclaimer, the term of this patent is extended or adjusted under 35 U.S.C. 154(b) by 7 days.

(21) Appl. No.: 16/750,968

(22) Filed: Jan. 23, 2020

(65) Prior Publication Data

US 2020/0253032 A1 Aug. 6, 2020

(30) Foreign Application Priority Data

Jan. 31, 2019 (JP) .............................. JP2019-016443

(51) Int. Cl.
*H05G 1/54* (2006.01)
*H05G 1/30* (2006.01)
*G01N 23/04* (2018.01)
*G01N 23/18* (2018.01)
*G01N 33/12* (2006.01)

(52) U.S. Cl.
CPC ............... *H05G 1/30* (2013.01); *G01N 23/04* (2013.01); *G01N 23/18* (2013.01); *H05G 1/54* (2013.01); *G01N 33/12* (2013.01)

(58) Field of Classification Search
CPC .. H05G 1/30; H05G 1/54; H05G 1/04; H05G 1/025; G01N 23/04; G01N 23/18; G01N 33/12

See application file for complete search history.

(56) References Cited

U.S. PATENT DOCUMENTS 6,491,428 B1 * 12/2002 Takanashi .............. A61B 6/035
378/199

FOREIGN PATENT DOCUMENTS

| GB | 2370634 A | 7/2002 |
| JP | H06-70145 U | 9/1994 |
| JP | 2003190136 A | 7/2003 |
| JP | 2009273781 A | 11/2009 |
| JP | 2009300379 A | 12/2009 |
| JP | 2018-155550 A | 10/2018 |

OTHER PUBLICATIONS

The extended European search report dated Jun. 16, 2020.

* cited by examiner

*Primary Examiner* — Courtney D Thomas
(74) *Attorney, Agent, or Firm* — Global IP Counselors, LLP

(57) ABSTRACT

An X-ray inspection device is configured to prevent water from flowing into areas of the X-ray inspection device during a washing operation. The X-ray inspection device is provided with an X-ray emitter, a cooler, a cooler cover, and an opening/closing member. The cooler cools the X-ray emitter. The cooler cover covers the cooler. Openings are formed in the cooler cover and, when open, provide interior-exterior air flow communication when the cooler is cooling the X-ray inspection device. An opening/closing member is configured for movement between an open orientation opening the opening and a closed orientation closing the openings formed in the cooler cover.

10 Claims, 14 Drawing Sheets

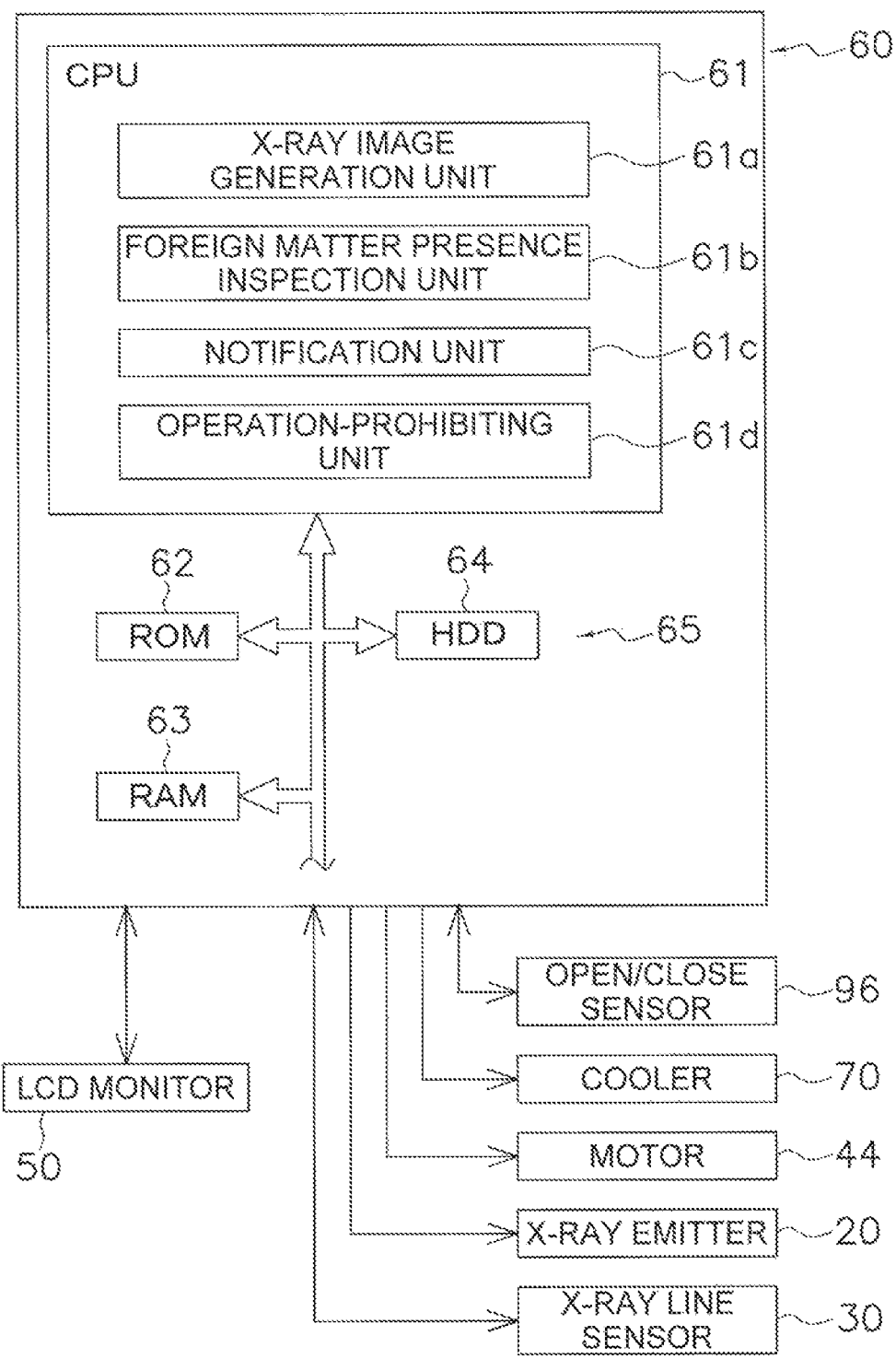
F I G. 3

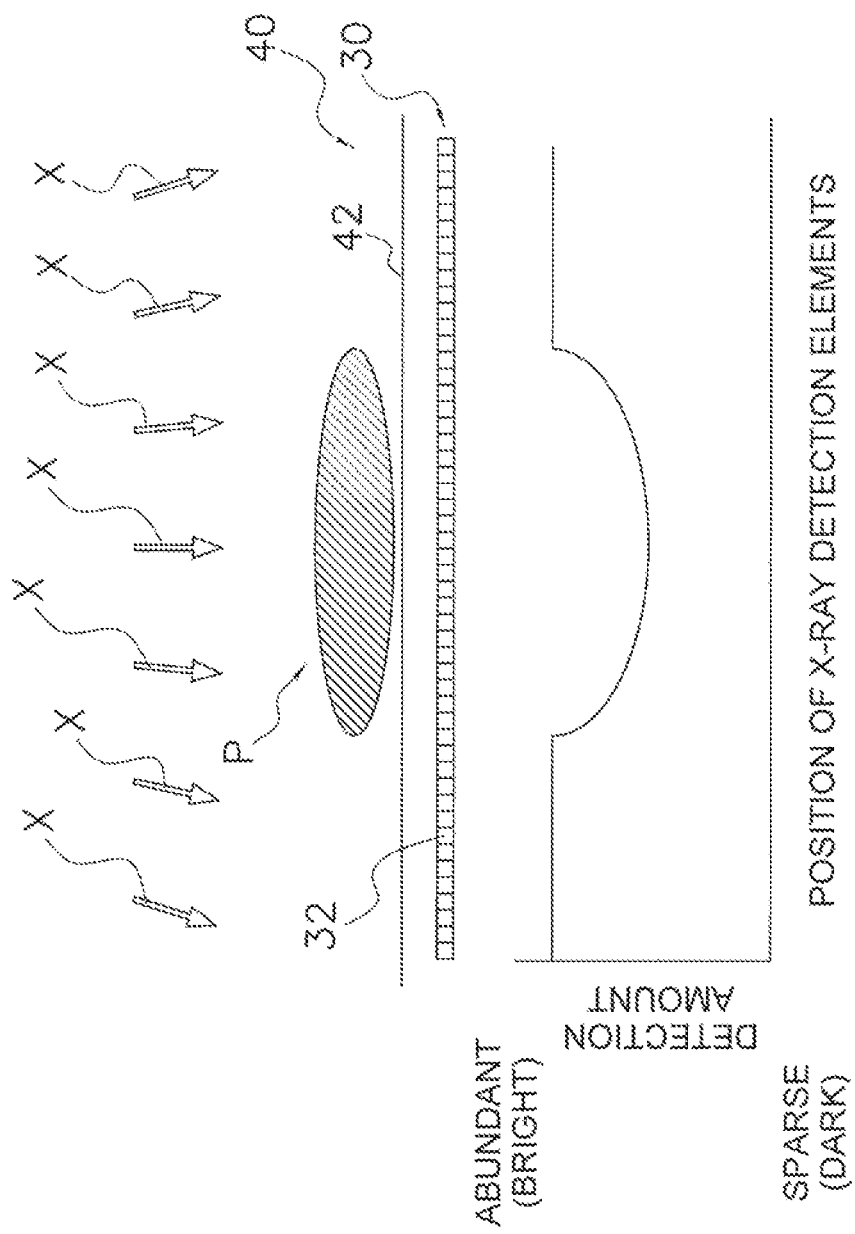
F I G. 8

X-RAY INSPECTION DEVICE

CROSS-REFERENCE TO RELATED APPLICATIONS

This U.S. non-provisional patent application claims priority under 35 U.S.C. § 119(a) to Japanese Patent Application No. 2019-016443, filed in Japan on Jan. 31, 2019, the entire contents of which are hereby incorporated herein by reference.

BACKGROUND ART

In the prior art there are known X-ray inspection devices provided with a cooler for cooling an X-ray source, etc., as in Japanese Laid-Open Patent Application No. 2018-155550. The cooler used in an X-ray inspection device is ordinarily covered with a cooler cover, as disclosed in Japanese Laid-Open Patent Application No. 2018-155550.

SUMMARY OF THE INVENTION

Problem to be Solved by the Invention

In X-ray inspection devices such as disclosed in Japanese Laid-Open Patent Application No. 2018-155550, washing may be required depending on the associated application thereof, and the following problems may occur during washing.

As indicated above, the cooler of an X-ray inspection device is ordinarily covered by a cooler cover, and is constructed such that the cooler cover hinders applying water directly to the cooler, etc., during washing. However, openings for taking in outside air and for exhausting air are provided to the cooler cover in order to dissipate heat. Consequently, when washing water and/or washing steam are applied to the cooler cover, water may flow through the openings into the interior of the cooler cover. When water enters the cooler cover from the openings, the cooler and/or various other devices housed in the housing of the X-ray inspection device may be adversely affected.

In order to prevent such problems from occurring, the operator who cleans the X-ray inspection device is required to carefully proceed with the washing operation so that water does not flow into the cooler cover from the opening, leading to a prolonged washing operation or other problems.

An object of the present invention is to provide an X-ray inspection device which is easy to wash and in which water does not readily flow into the device during the washing operation.

Solution to Problem

The X-ray inspection device according to a first aspect of the present invention includes an X-ray source, a cooler, a cooler cover, and an opening/closing member. The cooler cools the X-ray source. The cooler cover covers the cooler. The cooler cover has an opening formed therein via which the interior and exterior communicate. The opening/closing member opens and closes the opening formed in the cooler cover.

In the X-ray inspection device according to the first aspect of the present invention, the opening/closing member for opening and closing the opening of the cooler cover is provided to the opening of the cooler cover that is used to take in external air and supply the air to the cooler or to exhaust the air heated by the cooler to the exterior. Consequently, in the present X-ray inspection device, the possibility of water flowing into the cooler cover during the washing operation can be reduced. A cleaning operator can perform a cleaning operation without paying close attention to the inflow of water from the opening of the cooler cover, and cleaning time can therefore be reduced.

The X-ray inspection device according to a second aspect of the present invention is the X-ray inspection device of the first aspect, and furthermore includes an open/close sensor. The open/close sensor senses opening/closing of the opening with the opening/closing member.

In the X-ray inspection device according to the second aspect of the present invention, opening/closing of the opening is sensed by the open/close sensor, and it is therefore easy to monitor the occurrence of a mistake such as the opening being open when the opening should be closed, or conversely, the opening being closed when the opening should be open.

The X-ray inspection device according to a third aspect of the present invention is the X-ray inspection device of the second aspect, and furthermore includes an electronic controller that includes a notification unit. The notification unit provides, on the basis of a sensing result obtained by the open/close sensor, notification of information related to opening/closing of the opening with the opening/closing member.

In the X-ray inspection device according to the third aspect of the present invention, notification of information related to opening/closing of the opening with the opening/closing member is provided, and it is therefore possible to reduce the occurrence of a mistake such as when the opening being open when the opening should be closed, or conversely, the opening being closed when the opening should be open.

The X-ray inspection device according to a fourth aspect of the present invention is the X-ray inspection device of the third aspect, wherein, at least prior to a start of operation or at the time of the start of operation of the X-ray inspection device, the notification unit issues notification of information related to opening/closing of the opening with the opening/closing member.

In the X-ray inspection device according to the fourth aspect of the present invention, it is easy to suppress the incidence of situations in which the X-ray inspection device is operated with the opening closed even though the X-ray source needs to be cooled.

The X-ray inspection device according to a fifth aspect of the present invention is the X-ray inspection device of third or fourth aspect, wherein, at least at an end of operation of the X-ray inspection device or after the end of operation of the X-ray inspection device, the notification unit issues notification of information related to opening/closing of the opening with the opening/closing member.

In the X-ray inspection device according to a fifth aspect of the present invention, at the end of operation of the X-ray inspection device or after the end of operation of the X-ray inspection device when there is a possibility that the X-ray inspection device will be washed thereafter, notification of information related to opening/closing of the opening with the opening/closing member is issued. Accordingly, in the present X-ray inspection device, it is easy to suppress the incidence of situations in which the X-ray inspection device is washed with the opening left open.

The X-ray inspection device according to a sixth aspect of the present invention is the X-ray inspection device of any of the third to fifth aspects, wherein the notification unit issues notification that the X-ray inspection device is inoperable when the open/close sensor senses that the opening is closed with the opening/closing member.

In the X-ray inspection device according to the sixth aspect of the present invention, it is easy to suppress the incidence of situations in which the X-ray inspection device is operated with the opening closed even though the X-ray source needs to be cooled.

The X-ray inspection device according to a seventh aspect of the present invention is the X-ray inspection device of any of the second to sixth aspects, and furthermore includes an operation-prohibiting unit. The operation-prohibiting unit prohibits operation of the X-ray inspection device when the open/close sensor senses that the opening is closed with the opening/closing member.

In the X-ray inspection device according to the seventh aspect of the present invention, the X-ray inspection device cannot be operated with the opening closed, and it is therefore possible to suppress the incidence of problems such as overheating of the X-ray source and other components.

The X-ray inspection device according to an eighth aspect of the present invention is the X-ray inspection device of any of the first to seventh aspects, wherein the cooler cover defines a rectangular parallelepiped or semi-cylindrical space.

In the X-ray inspection device according to the eighth aspect of the present invention, the cooler cover can be realized with a simple shape.

The X-ray inspection device according to a ninth aspect of the present invention is the X-ray inspection device of any of the first to eighth aspects, and further includes a resistance mechanism. The resistance mechanism inhibits opening actuation of the opening/closing member, which is closing the opening.

In the X-ray inspection device according to the ninth aspect of the present invention, opening actuation of the opening/closing member is inhibited by the resistance mechanism, and the configuration is therefore highly convenient in that it is possible to suppress the opening/closing member from readily opening and water flowing into the interior during washing of the X-ray inspection device, even if the opening/closing member is not secured by some means.

The X-ray inspection device according to a tenth aspect of the present invention is the X-ray inspection device of the ninth aspect, wherein the resistance mechanism maintains, against water discharge equivalent to IP69K, a state in which the opening is closed with the opening/closing member, which closes the opening.

In the X-ray inspection device according to the tenth aspect of the present invention, the state in which the opening is closed with the opening/closing member is maintained even when water discharge equivalent to IP69K is performed. Consequently, even when high-pressure washing of the X-ray inspection device is performed for the purpose of disinfection or sterilization, it is possible to prevent the opening/closing member from readily opening and water flowing into the interior during washing of the X-ray inspection device.

IP69K is a protection regulation against high temperature/high pressure water, which is defined by German Standard DIN 40050 PART 9 of the German Industrial Standard. IP69K equivalent water discharge means that water at 80° C. is discharged from a distance of 10 to 15 cm at a water pressure of 80 to 100 bar at a rate of 14 to 16 L/min from a nozzle of predetermined shape.

Effect of Invention

In the X-ray inspection device of the present invention, the possibility of water flowing into the X-ray inspection device during a washing operation can be reduced.

BRIEF DESCRIPTION OF THE DRAWINGS

FIG. 3 is a simplified control block diagram of the X-ray inspection device of FIG. 2;

FIG. 8 is a graph showing an example of the amount of transmission X-rays detected by an X-ray detection element in the X-ray inspection device of FIG. 2;

DESCRIPTION OF EMBODIMENTS

Embodiments of the X-ray inspection device according to the present invention will now be described.

The embodiments of the X-ray inspection device described below are merely examples. It shall be apparent that various modifications can be made to the embodiments of the present disclosure without departing from the spirit and scope of the present disclosure.

First Embodiment

The X-ray inspection device 100 of a first embodiment of the present invention is described below with reference to the drawings.

(1) Overall Description

Figure 1:
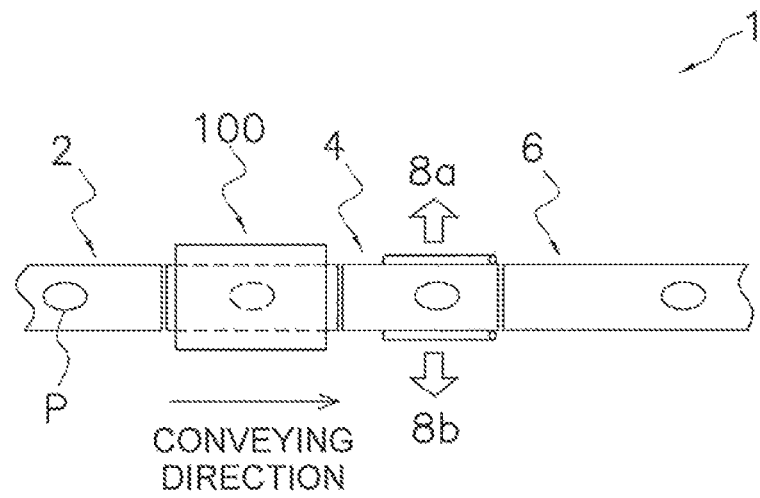
FIG. 1 is a simplified view of an inspection system that includes the X-ray inspection device according to an embodiment of the present invention.
Figure 2:
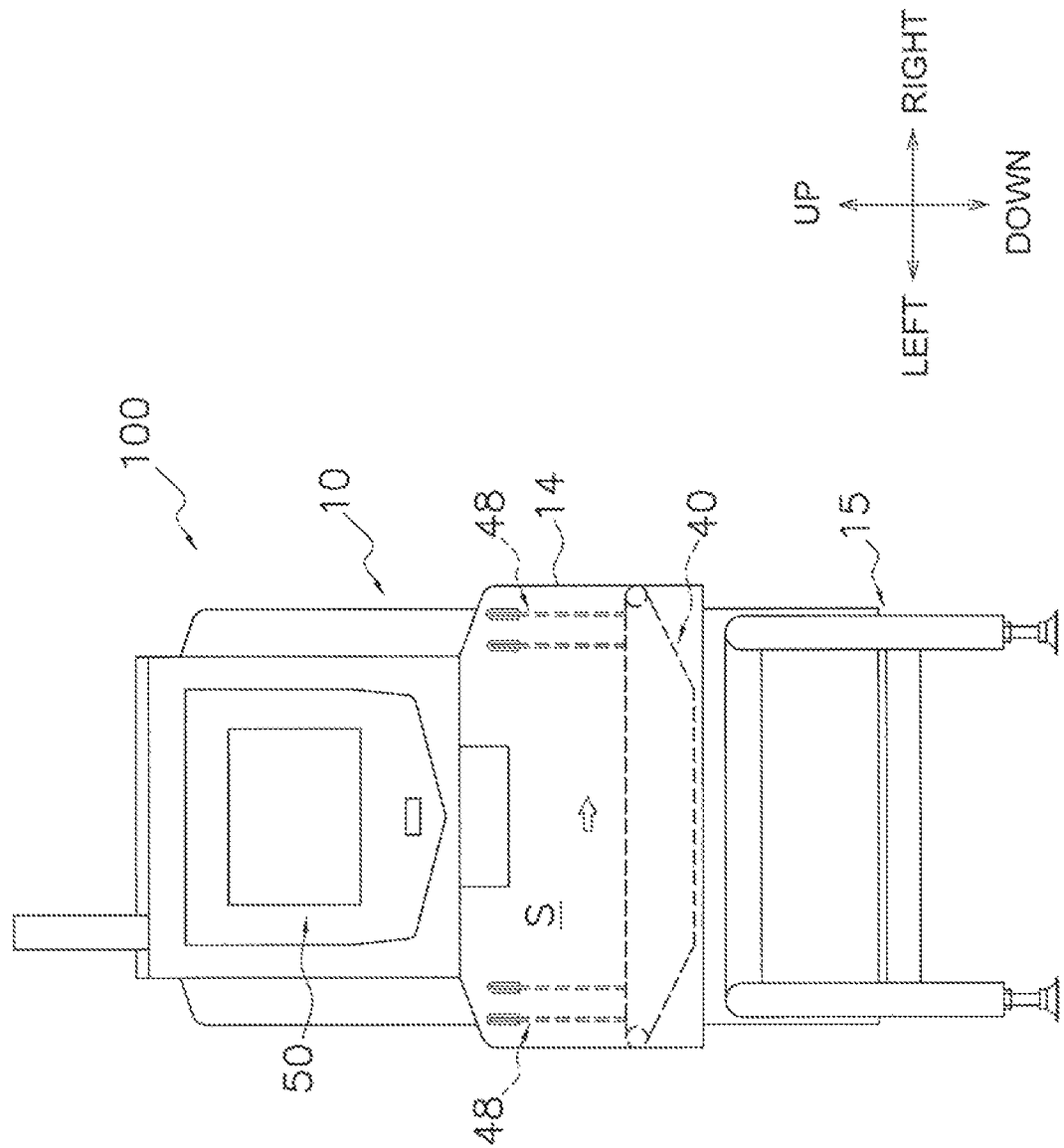
FIG. 2 is a simplified front view of the X-ray inspection device according to the first embodiment of the present invention.
Figure 4:
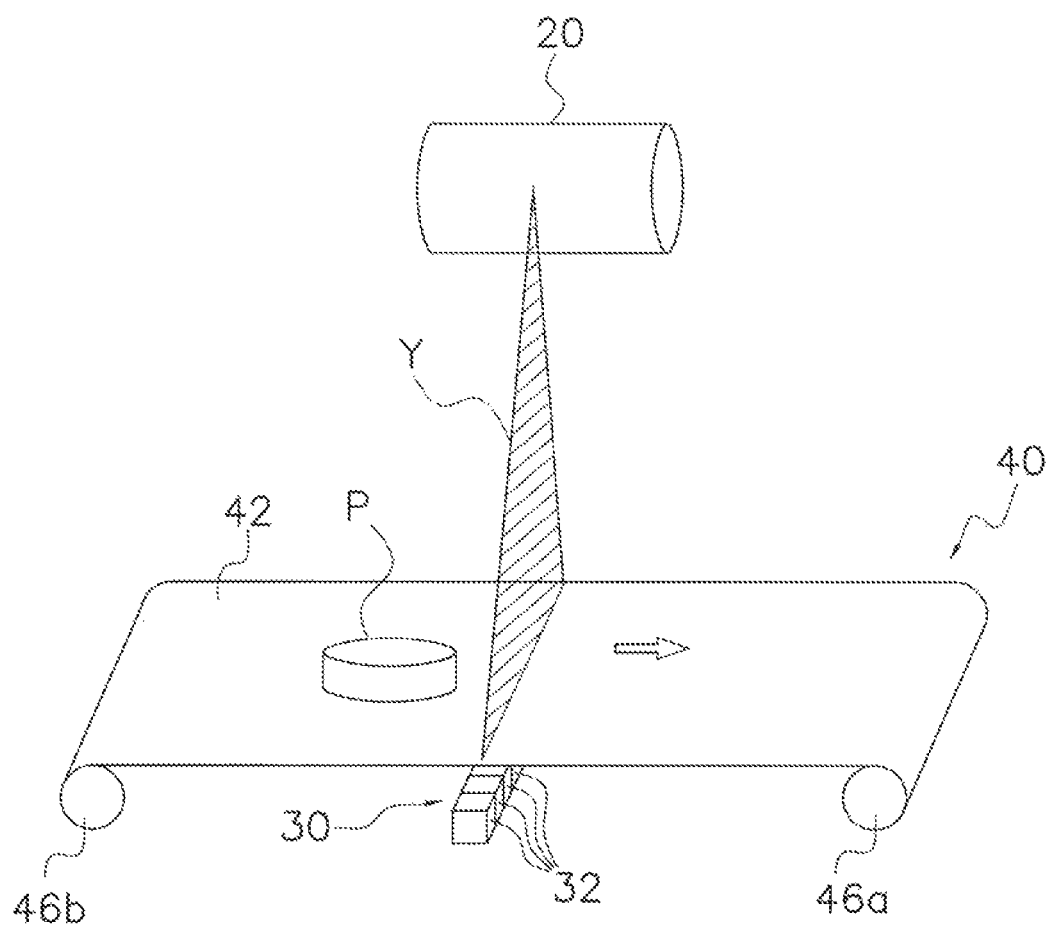
FIG. 4 is a simple configuration diagram of the interior of a shield box of the X-ray inspection device of FIG. 2.
Figure 4:
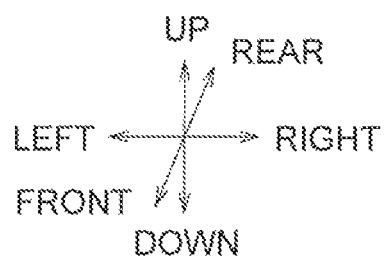
Figure 5A:
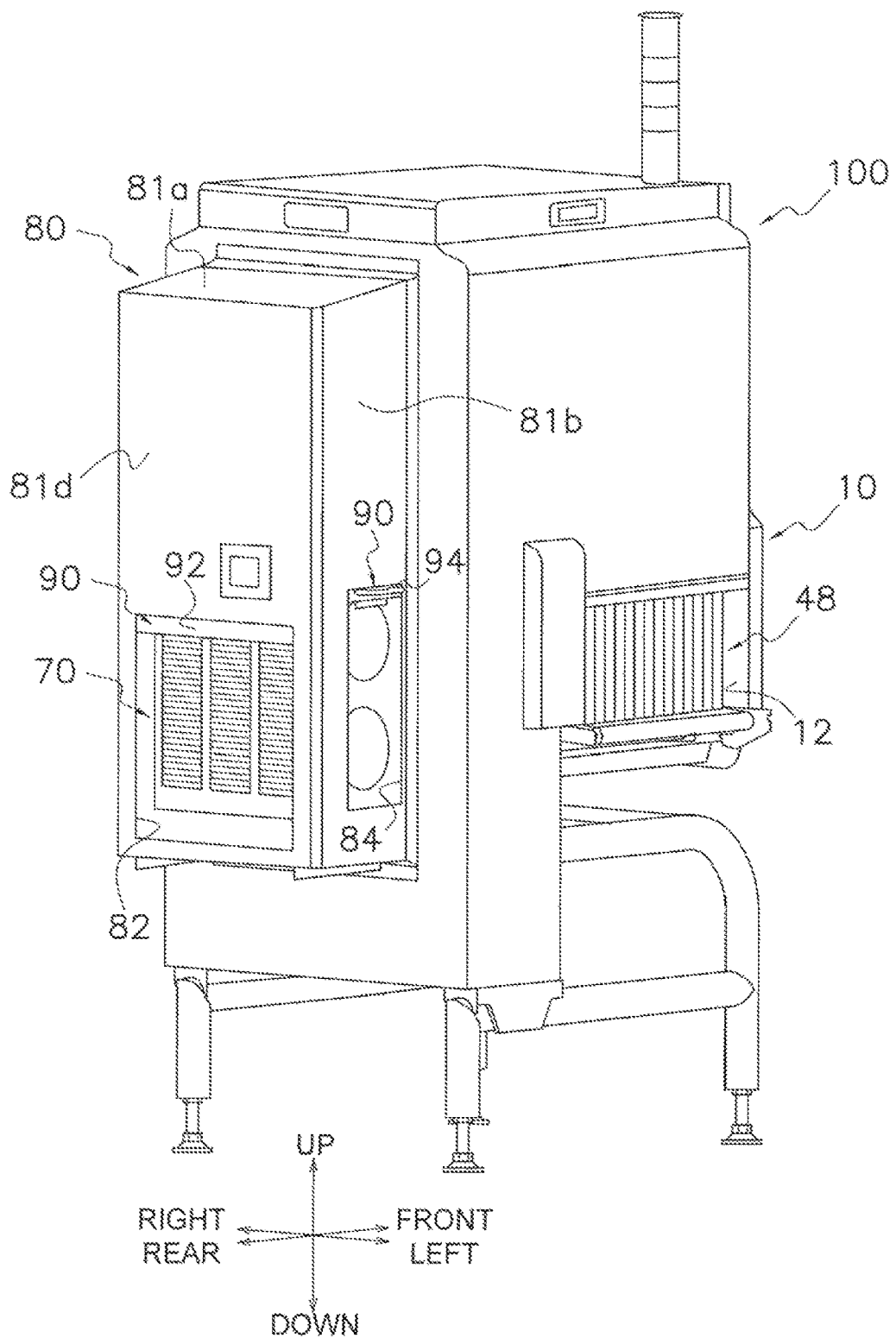
FIG. 5A is a simplified perspective view as seen diagonally from the rear of the X-ray inspection device of FIG. 2, and depicts a state in which an opening/closing member provided to openings of the cooler cover is open.
Figure 5B:
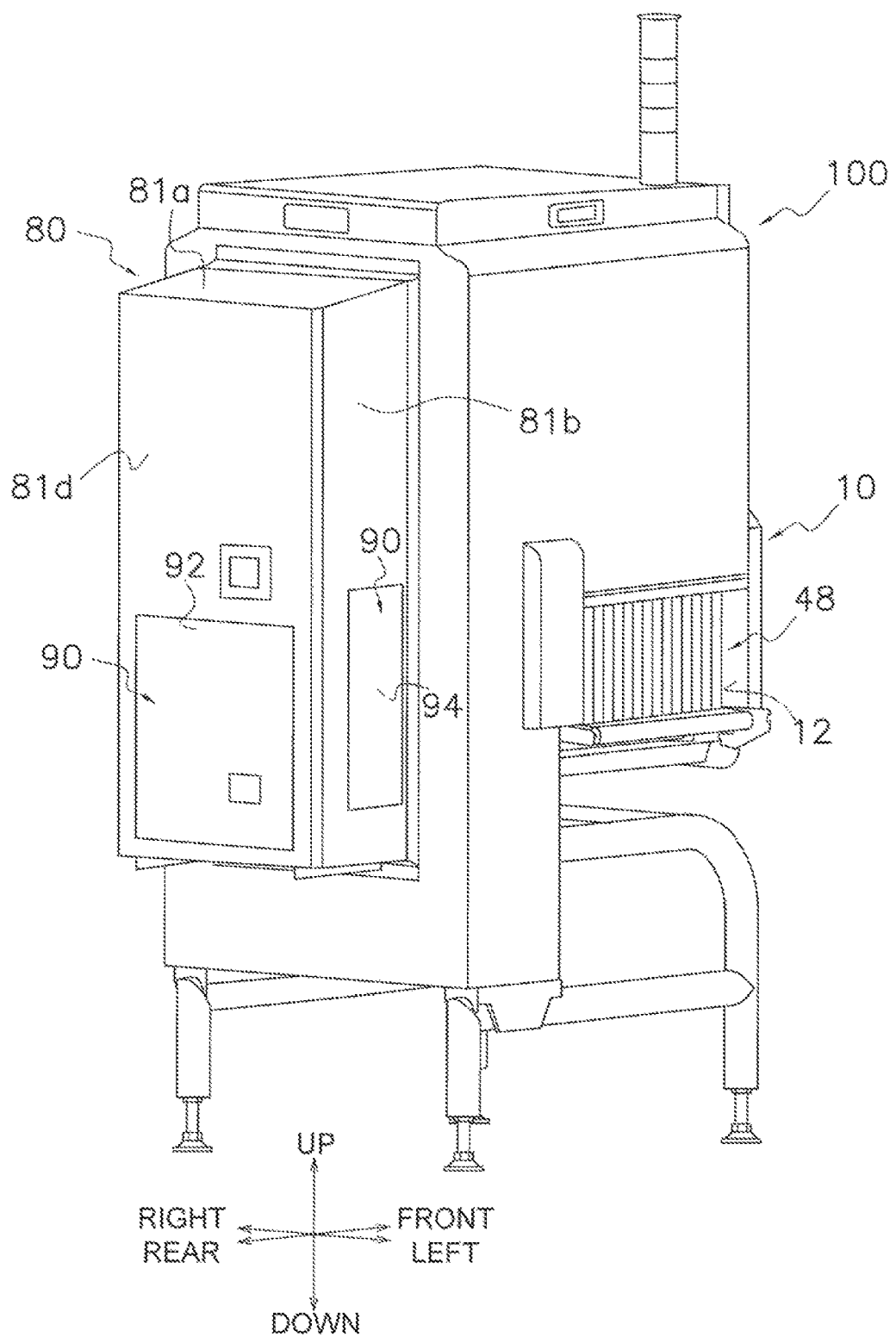
FIG. 5B is a simplified perspective view as seen diagonally from the rear of the X-ray inspection device of FIG. 2, and depicts a state in which an opening/closing member provided to the openings of the cooler cover is closed.
Figure 6A:
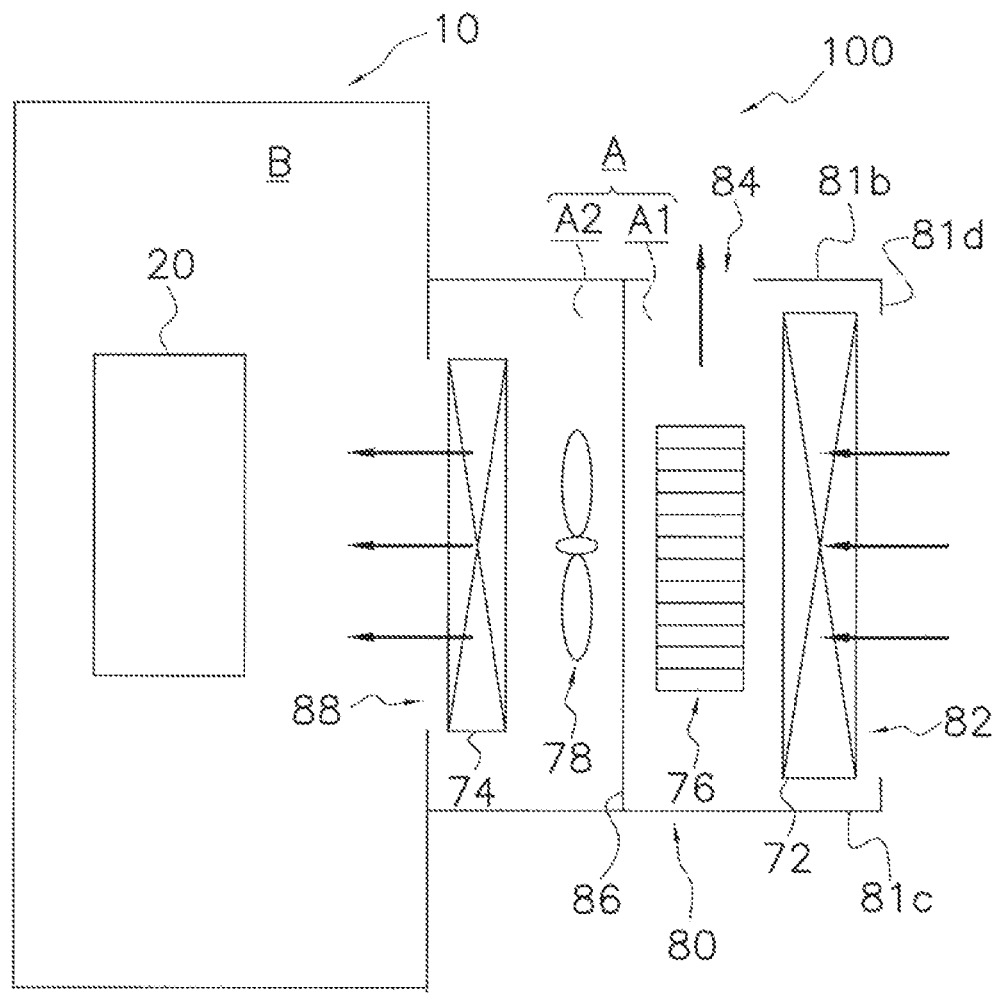
FIG. 6A is a plan view that schematically shows the interior of the X-ray inspection device of FIG. 2, and depicts only the X-ray emitter and some of the equipment of the cooler.
Figure 6B:
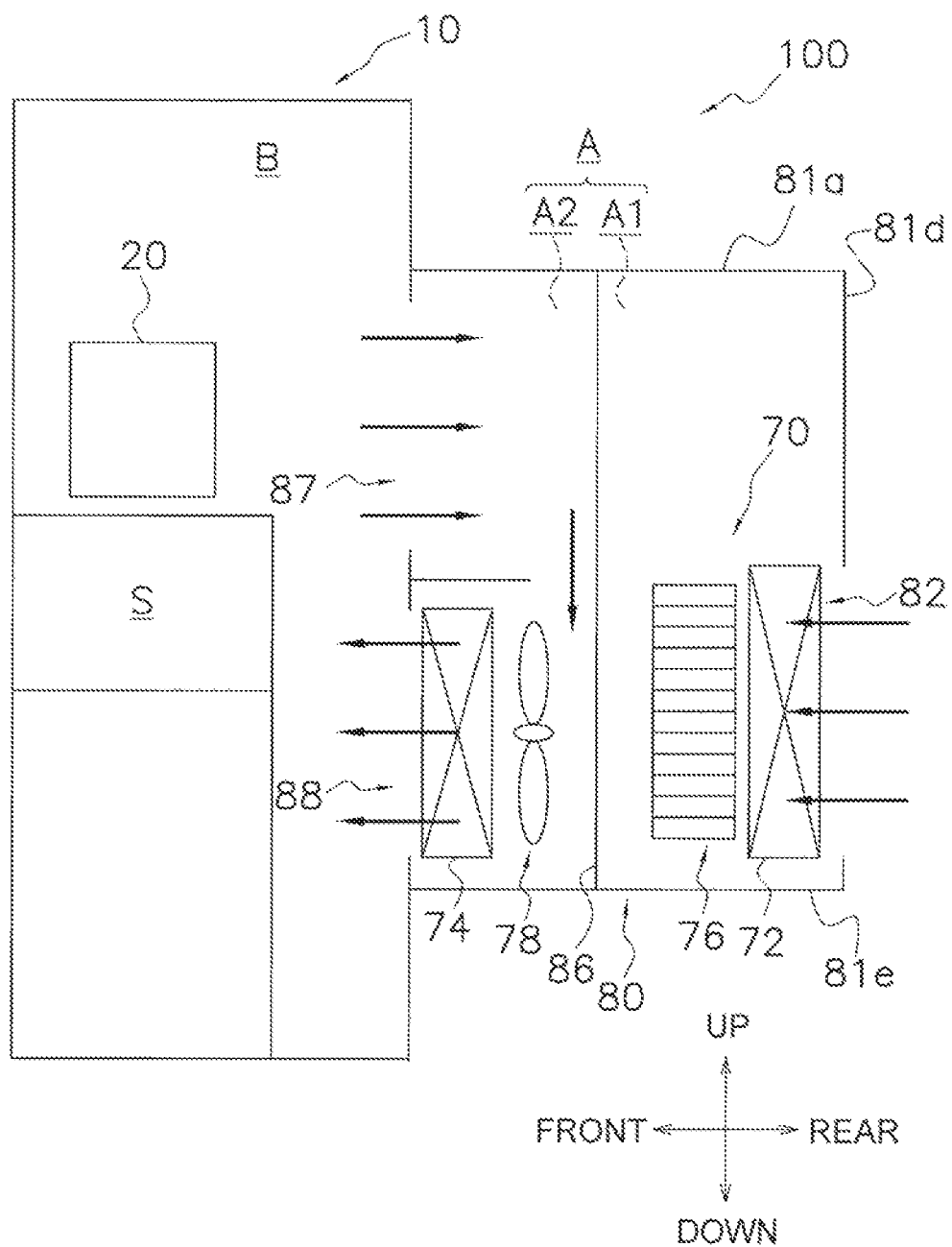
FIG. 6B is a side view that schematically shows the interior of the X-ray inspection device of FIG. 2, and depicts only the X-ray emitter and some of the equipment of the cooler.
Figure 7:
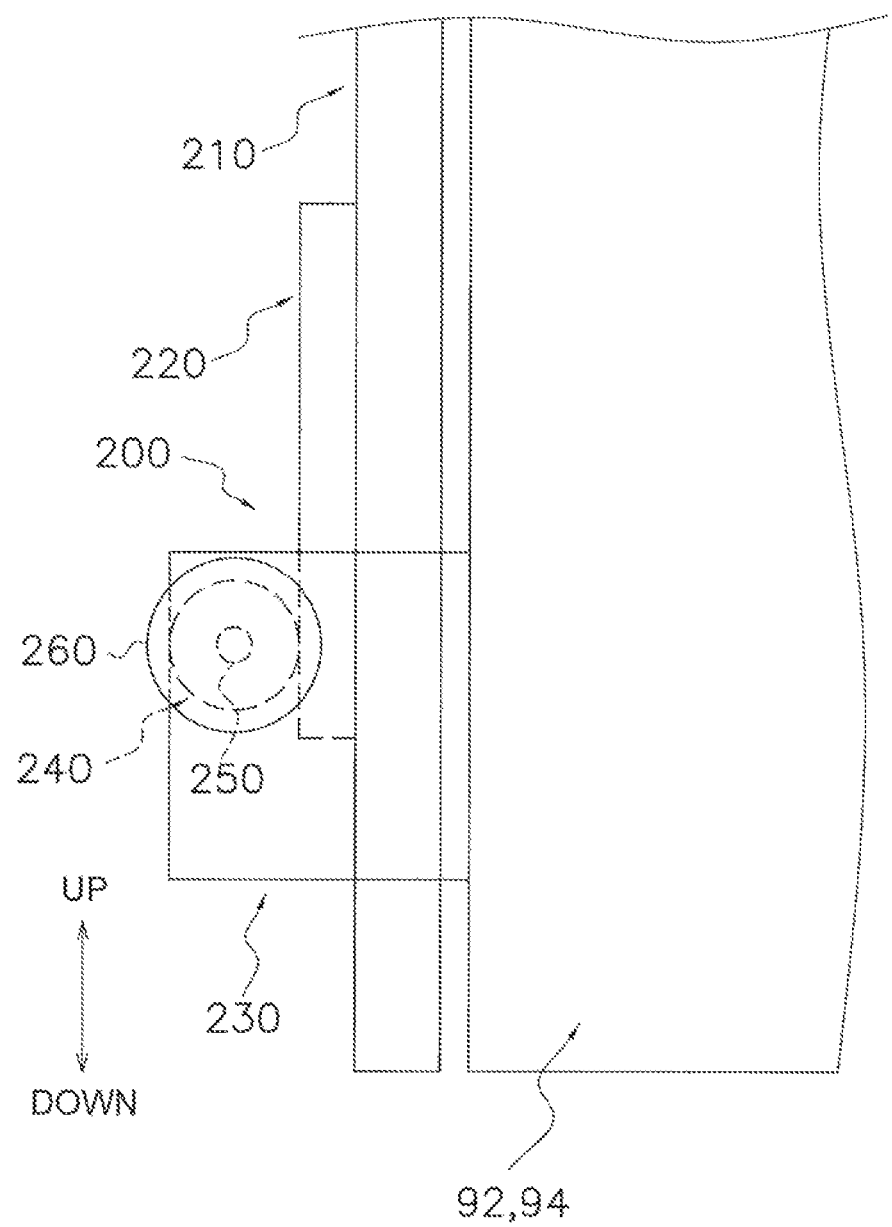
FIG. 7 is a schematic view of the resistance mechanism provided to the opening/closing member disposed in the openings of the cooler cover of FIG. 5A.
Figure 9A:
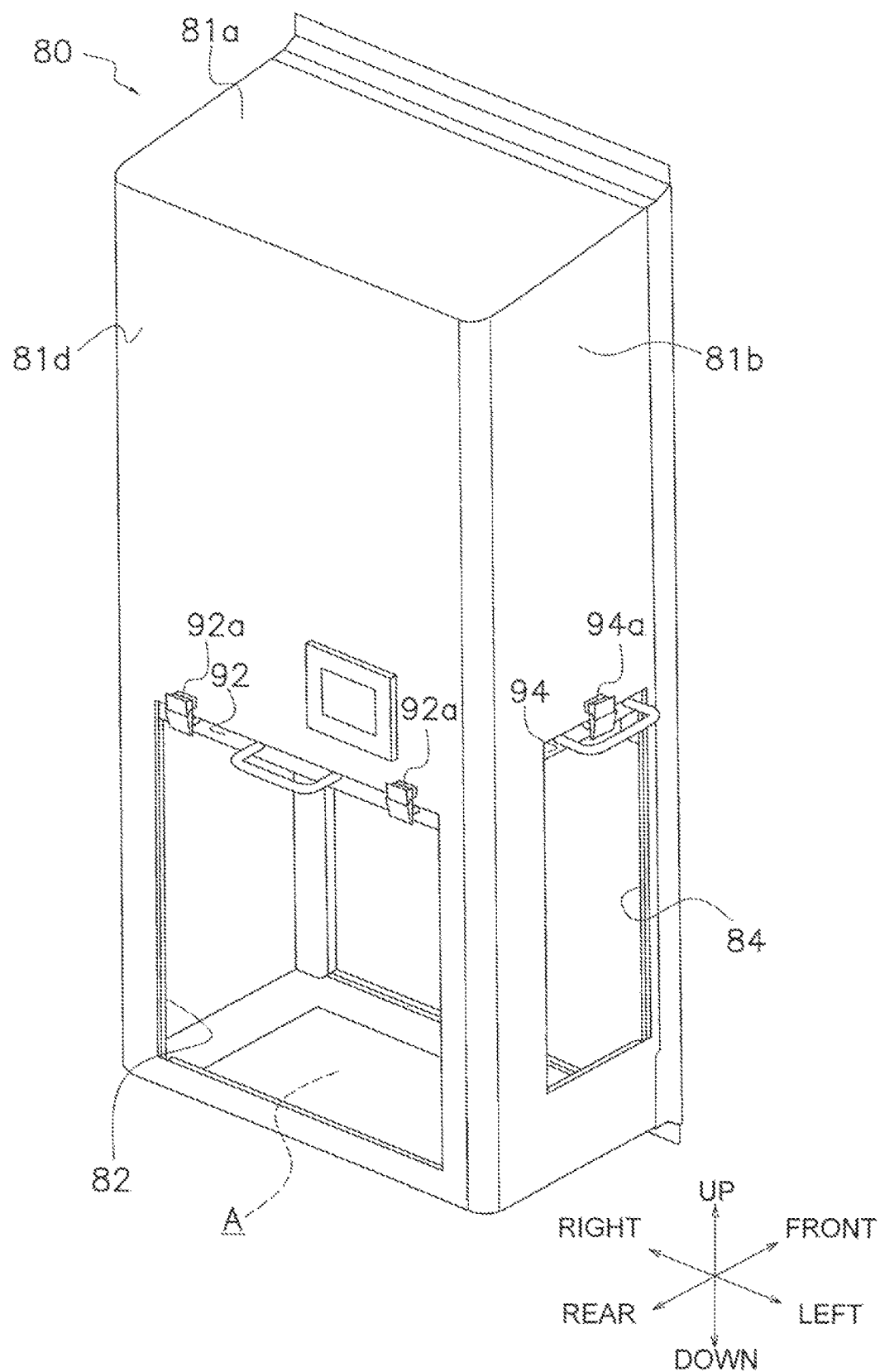
FIG. 9A is a perspective view of the external appearance of the cooler cover of the X-ray inspection device of FIG. 2, and depicts a state in which the opening/closing member provided to the openings of the cooler cover is open.
Figure 9B:
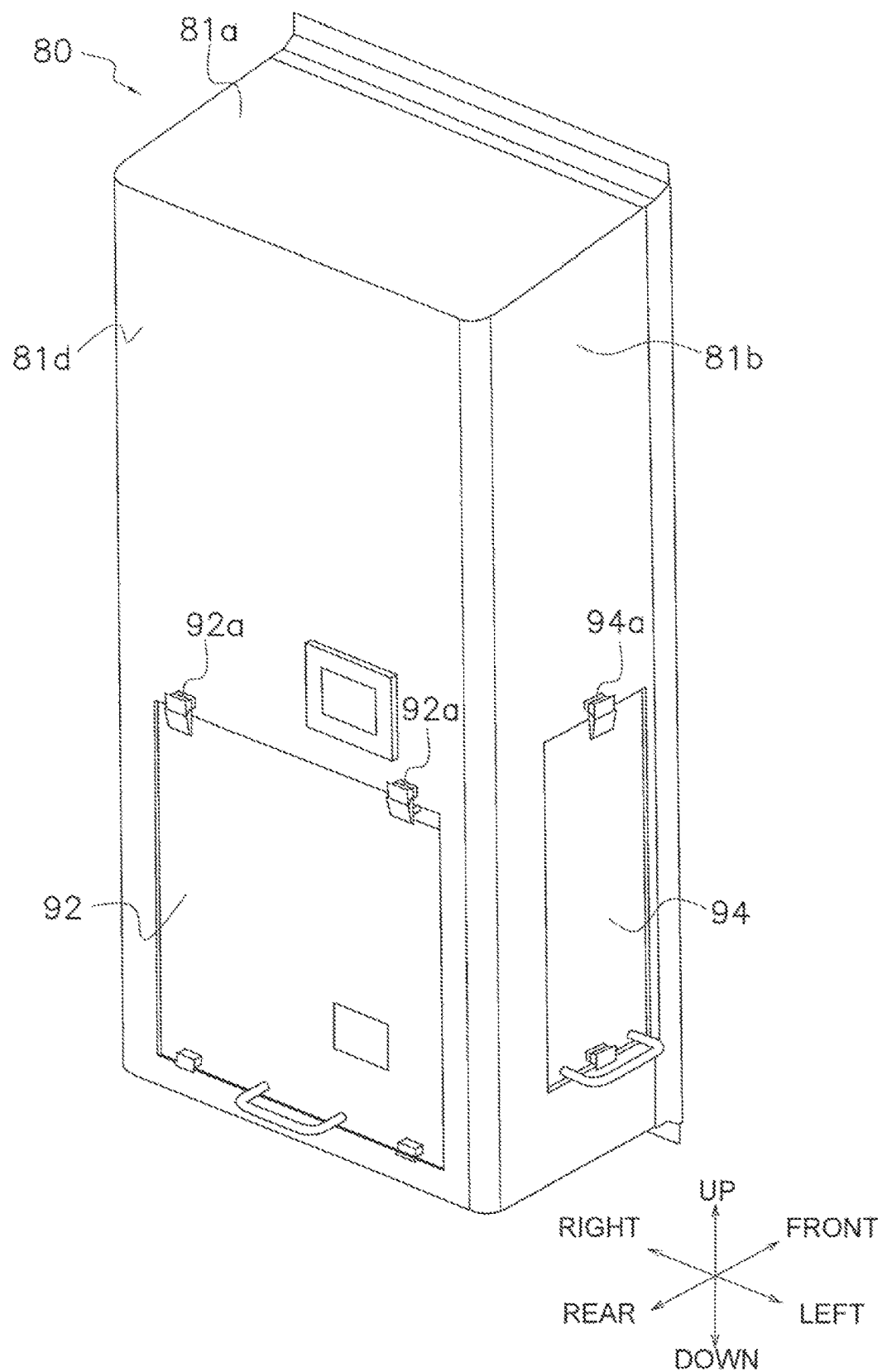
FIG. 9B is a perspective view of the external appearance of the cooler cover of the X-ray inspection device of FIG. 2, and depicts a state in which the opening/closing member provided to the openings of the cooler cover is closed.

FIG. 1 is a simplified view of an inspection system 1 that includes the X-ray inspection device 100 according to the first embodiment of the present invention. FIG. 2 is a simplified front view of the X-ray inspection device 100. FIG. 3 is simplified control block diagram of the X-ray inspection device 100. FIG. 4 is a simple configuration diagram of the interior of a shield box 10 of the X-ray inspection device 100. FIGS. 5A and 5B are simplified perspective views of the X-ray inspection device 100 as seen diagonally from the rear. FIG. 5A depicts a state in which the opening/closing member 90 provided to openings 82, 84 of the cooler cover 80 is open. FIG. 5B depicts a state in which the opening/closing member 90 provided to the openings 82, 84 of the cooler cover 80 is closed. FIG. 6A is a plan view that schematically shows the interior of the X-ray inspection device 100, and depicts the cooler cover 80 and the shield box 10, as well as only the X-ray emitter 20 and some of the equipment of the cooler 70 therein. FIG. 6B is a side view that schematically shows the interior of the X-ray inspection device 100, and depicts the cooler cover 80 and the shield box 10, as well as only the X-ray emitter 20 and some of the equipment of the cooler 70 therein. FIG. 7 is a schematic view of the resistance mechanism 200 provided to the opening/closing member 90 disposed in the openings 82, 84 of the cooler cover 80. FIG. 8 is a graph showing an example of the transmission amount of X-rays detected by an X-ray detection element 32 of the X-ray line sensor 30 in the X-ray inspection device 100. FIGS. 9A and 9B are perspective views of the external appearance of the cooler cover 80 of the X-ray inspection device 100. FIG. 9A depicts a state in which the opening/closing member 90 provided to the openings 82, 84 of the cooler cover 80 is open. FIG. 9B depicts a state in which the opening/closing member 90 provided to the openings 82, 84 of the cooler cover 80 is closed.

The X-ray inspection device 100 is incorporated into the inspection system 1, and is used for inspecting an article P. The type of article P to be inspected by the inspection system 1 is e.g., chicken or another food product but is not limited to. The X-ray inspection device 100 performs a quality inspection of the article P on the basis of an X-ray image obtained by emitting X-rays at the incoming article P. In the present embodiment, the X-ray inspection device 100 inspects for foreign matter in the article P, but the type of quality inspection is not limited to. Inspection for foreign matter is an inspection of whether the article P has been contaminated with foreign matter.

The X-ray inspection device 100 is washed using water periodically or at any times. Consequently, the X-ray inspection device 100 is preferably designed so that water does not penetrate the interior of the X-ray inspection device 100, even with, e.g., water discharge equivalent to IP69K. IP69K is a protection regulation for high temperature/high pressure water, which is defined by German Standard DIN 40050 PART 9 of the German Industrial Standard. IP69K equivalent water discharge means that water at 80° C. is discharged from a distance of 10 to 15 cm at a water pressure of 80 to 100 bar at a rate of 14 to 16 L/min from a nozzle of a predetermined shape defined by the standard. The water-proofness performance of the X-ray inspection device 100 is not required to be established so as to satisfy the IP69K standard, and may be established with consideration given to actual washing conditions of the X-ray inspection device 100.

The inspection system 1 has a first conveyor 2, the X-ray inspection device 100, a sorting device 4, and a second conveyor 6 (see FIG. 1). In the inspection system 1, the first conveyor 2 conveys the article P to the X-ray inspection device 100. In the X-ray inspection device 100, the article P is inspected for foreign matter. The result of inspecting for foreign matter by the X-ray inspection device 100 is transmitted to the sorting device 4 disposed downstream from the X-ray inspection device 100. The sorting device 4 sends the article P which has been determined not contain foreign matter to the second conveyor 6. The sorting device 4 sends the article P which has been determined by the X-ray inspection device 100 to contain foreign matter to defective-product holding conveyors 8a, 8b (see FIG. 1).

The X-ray inspection device 100 mainly has a shield box 10, an X-ray emitter 20, an X-ray line sensor 30, a conveyor mechanism 40, a shielding curtain 48, an LCD monitor 50, a cooler 70, a cooler cover 80, an opening/closing member 90, a resistance mechanism 200, an open/close sensor 96, and an electronic controller 60 (also referred to as the controller 60), as shown in FIGS. 2 to 7.

(2) Detailed Description

The X-ray inspection device 100 is described in detail below.

The terms "up," "down," "left," "right," "fore (front)," "rear (back)," and other expressions may be used below for convenience of description. These expressions, unless otherwise particularly stated, follow the directions indicated by the arrows in the drawings. In the present embodiment, the direction in which the article P is conveyed is the lateral direction, and the lengthwise direction of the X-ray line sensor 30 is the longitudinal direction.

(2-1) Shield Box

The shield box 10 houses the X-ray emitter 20, the X-ray line sensor 30, the controller 60, and other equipment. The shield box 10 covers an inspection space S. The inspection space S is a space in which X-rays emitted by the X-ray emitter 20 are emitted at the article P conveyed by the conveyor mechanism 40. The shield box 10 is supported by a leg frame 15 disposed below the shield box 10, as shown in FIG. 2.

The shield box 10 has an opening 12 on the left and right side surfaces, as shown in FIGS. 5A and 5B. It is through the openings 12 that the article P to be inspected is conveyed in and out. The article P is conveyed by the conveyor mechanism 40 from the opening 12 on the entrance side into the inspection space S inside the shield box 10, and conveyed out from the opening 12 on the exit side to the exterior of the shield box 10. In the present embodiment, the article P discharged by the first conveyor 2 is conveyed from the left-side opening 12 into the shield box 10, and conveyed out from the right-side opening 12 to the exterior of the shield box 10 and delivered to the sorting device 4.

A shielding curtain 48 is provided to the openings 12, which serve as a conveyance entrance and exit of the article P, in order to suppress X-ray leakage to the exterior of the shield box 10 (see FIG. 2). When the article P is conveyed into the shield box 10 and when the article P is conveyed out from the shield box 10, the shielding curtain 48 is pushed open by the article P, which makes contact with the shielding curtain 48.

A front panel 14 that can be opened and closed is provided to the lower front part of the shield box 10 (see FIG. 2). A maintenance operator rotates the front panel 14 so that the upper side of the front panel 14 is tilted forward, and opens the front panel 14, whereby maintenance of the shielding curtain 48 and/or the conveyor mechanism 40 disposed in the inspection space S can be performed.

An LCD monitor 50 is disposed on the upper front part of the shield box 10, as shown in FIG. 2. A power switch and other switches are also disposed on the upper front part of the shield box 10.

The cooler cover 80 is mounted on the back of the shield box 10, as shown in FIG. 5A. The internal space A surrounded by the cooler cover 80 and a first space B of the shield box 10 are in communication with each other via an intake port 87 and a blow-out port 88. The internal space A of the cooler cover 80 is a space surrounded by a top plate 81a, a left-side plate 81b, a right-side plate 81c, a rear-side plate 81d, and a bottom plate 81e of the cooler cover 80 (see FIGS. 5A, 6A, and 6B). The first space B of the shield box 10 houses the X-ray emitter 20 and/or equipment (e.g., an electronic board (not shown)) that emits heat other than the X-ray emitter 20 (see FIGS. 6A and 6B).

(2-2) X-Ray Emitter

The X-ray emitter 20 is an X-ray source that emits X-rays.

The X-ray emitter 20 is disposed at the center in the lateral-direction inside the shield box 10, as shown in FIG. 6A. The X-ray emitter 20 is disposed above the inspection space S through which the conveyor mechanism 40 conveys the article P, as shown in FIG. 6A. In other words, the X-ray emitter 20 is disposed above a conveyor belt 42 of the conveyor mechanism 40, as shown in FIG. 4.

The X-ray emitter 20 emits X-rays at the X-ray line sensor 30 disposed below the conveyor belt 42 (see FIG. 4). In other words, the X-ray emitter 20 emits X-rays toward the article P, which is conveyed by the conveyor mechanism 40 and passes above the X-ray line sensor 30. The X-ray emitter 20 emits X-rays so as to spread out in a direction (in this case, the longitudinal direction) orthogonal to the conveying direction of the article P conveyed by the conveyor mechanism 40. In other words, the X-ray emitter 20 emits X-rays so as to spread out in the width direction of the conveyor belt 42. The emission range Y of the X-rays emitted by the X-ray emitter 20 is substantially fan-shaped.

(2-3) X-Ray Line Sensor

The X-ray line sensor 30 is an X-ray detector for detecting X-rays.

The X-ray line sensor 30 is disposed below the inspection space S through which the conveyor mechanism 40 conveys the article P, as shown in FIG. 4. In other words, the X-ray line sensor 30 is disposed below the conveyor belt 42 of the later-described conveyor mechanism 40.

The X-ray line sensor 30 mainly has numerous X-ray detection elements 32, as shown in FIG. 4. The X-ray detection elements 32 of the X-ray line sensor 30 are disposed so as to be lined up in a direction that intersects the conveying direction of the article P on the conveyor mechanism 40. In this particular case, the X-ray detection elements 32 are disposed so as to be lined up in the longitudinal direction orthogonal to the conveying direction of the article P on the conveyor mechanism 40.

The X-ray line sensor 30 detects X-rays (transmission X-rays) that have been transmitted through the article P. Specifically, the X-ray detection elements 32 of the X-ray line sensor 30 detect the X-ray dose (amount of transmission X-rays) transmitted through the article P. Each of the X-ray detection elements 32 outputs an X-ray transmission signal that represents a voltage that corresponds to an intensity of detected transmission X-rays (i.e., amount of transmission X-rays). An electronic controller 60 (described below) receives the X-ray transmission signal outputted by the X-ray line sensor 30, and generates an X-ray image on the basis of the X-ray transmission signal.

FIG. 8 is a graph showing an example of the amount of transmission X-rays detected by the X-ray detection elements 32 of the X-ray line sensor 30. The horizontal axis of the graph corresponds to the positions of the X-ray detection elements 32. The horizontal axis of the graph also corresponds to the distance in the horizontal direction orthogonal to the conveying direction of the conveyor mechanism 40. The vertical axis of the graph represents the amount of transmission X-rays detected by the X-ray detection elements 32. In the X-ray image generated by the controller 60 on the basis of the detection results of the X-ray line sensor 30, areas with a high amount of transmission X-rays are displayed brightly (lightly), and areas with a low amount of transmission X-rays are displayed darkly (densely). That is, the brightness (intensity) of the X-ray image corresponds to the detected amount of transmission X-rays.

(2-4) Conveyor Mechanism

The conveyor mechanism 40 receives the article P conveyed into the X-ray inspection device 100 by the first conveyor 2 of the inspection system 1, conveys the article P so as to pass through the inspection space S, and delivers the article P to the second conveyor 6 on the downstream side of the X-ray inspection device 100. The type of conveyor mechanism 40 is not limited; in the present embodiment, the conveyor mechanism 40 is a belt conveyor. The conveyor mechanism 40 is disposed so as to extend through the two openings 12 formed on the left side and right side of the shield box 10, and the conveyance path through which the conveyor mechanism 40 conveys the article P extends through the shield box 10.

The conveyor mechanism 40 mainly includes the conveyor belt 42, a motor 44, a drive roller 46a, and a driven roller 46b (see FIGS. 2 and 4). The conveyor belt 42 is an endless belt which is wrapped around the drive roller 46a and the driven roller 46b. The motor 44 drives to rotate the drive roller 46a. The conveyor mechanism 40 rotates the drive roller 46a with the motor 44 to thereby drive the conveyor belt 42 and convey the article P on the conveyor belt 42.

(2-5) Shielding Curtain

The shielding curtain 48 is a member for preventing leakage of X-rays to the exterior of the inspection space S. The shielding curtain 48 is made of, e.g., rubber containing tungsten. However, the material of the shielding curtain 48 is not limited to rubber containing tungsten, and may be, e.g., stainless steel.

The shielding curtain 48 is provided to the openings 12 at the entrance and exit of the article P in two rows along the conveying direction of the article P (see FIG. 2). However, the number of rows of the shielding curtain 48 is an example and is not limited to two rows; the number may be one row or three rows. From the viewpoint of preventing leakage of X-rays, a plurality of rows of the shielding curtain 48 are preferably provided along the conveying direction of the article P.

(2-6) LCD Monitor

The LCD monitor 50 is a full-dot liquid crystal display having an information display function. The LCD monitor 50 has a touch panel function in addition to the information display function.

The LCD monitor 50 displays the X-ray image generated by the controller 60 and the result of inspection for foreign matter obtained by the controller 60. The LCD monitor 50 also displays settings of the X-ray inspection device 100 and a screen that prompts for inspection parameters, etc., to be inputted.

The LCD monitor 50 furthermore displays information related to the opening and closing (may be referred to hereinbelow as open/close-related information for simplicity of description) of the openings 82, 84 of the cooler cover 80 by the opening/closing member 90 in response to an instruction of a notification unit 61c of the controller 60. The content of the opening/closing-related information displayed on the LCD monitor 50 is described later.

(2-7) Cooler and Cooler Cover

The cooler 70 is a cooling device for cooling air in the first space B of the shield box 10 of the X-ray inspection device 100. The cooler 70 cools the air in the first space B to thereby cool the X-ray emitter 20 disposed in the first space B (see FIG. 6B). The cooler 70 cools the air in the first space B to thereby also cool heating-emitting equipment other than the X-ray emitter 20 disposed in the first space B. The heat-emitting equipment other than the X-ray emitter 20 includes, e.g., an electronic board (not shown).

The cooler cover 80 is a cover for covering the cooler 70.

The details are described hereinbelow.

(2-7-1) Cooler Cover

The cooler cover 80 is mounted on the rear side of the shield box 10 of the X-ray inspection device 100, and is a member for covering the cooler 70. Various pieces of equipment of the cooler 70 are housed in the internal space A (see FIG. 6A) defined by the cooler cover 80. The internal space A is a space surrounded by a top plate 81a, a left-side plate 81b, a right-side plate 81c, a rear-side plate 81d, and a bottom plate 81e of the cooler cover 80 (see FIGS. 5A, 6A, and 6B). Not all of the equipment of the cooler 70 is required to be disposed in the internal space A. In a case when the cooler 70 can demonstrate the function thereof, some of the equipment of the cooler 70 can be disposed in the first space B of the shield box 10.

The internal space A defined by the cooler cover 80 is partitioned by a partition member 86 into a first internal space A1 and a second internal space A2 (see FIGS. 6A and 6B). The partition member 86 is a member for suppressing the flow of air between the air in the first internal space A1 and the air in the second internal space A2. The first internal space A1 and second internal space A2 are described later.

Openings 82, 84 are formed in the cooler cover 80 to provide communication between the interior and exterior. The opening 82 functions as an intake port for air from the exterior to the interior of the cooler cover 80. The opening 84 functions as an exhaust port for air from the interior of the cooler cover 80 to the exterior. The opening 82 is formed in the rear-side plate 81d of the cooler cover 80. The opening 84 is formed in the left-side plate 81b of the cooler cover 80. The positions in which the openings 82, 84 are formed as shown herein are merely an example, and can be established, as appropriate. In FIGS. 5A and 5B, the shape of the openings 82, 84 are depicted as being rectangular, but the shape of the openings 82, 84 depicted in FIGS. 5A and 5B is merely an example; any shape can be used. The opening/closing member 90 for opening and closing the openings 82, 84 is provided to the openings 82, 84 of the cooler cover 80. Specifically, a first door 92 of the opening/closing member 90 is disposed in the opening 82 of the cooler cover 80 in order to open and close the opening 82. A second door 94 of the opening/closing member 90 is disposed in the opening 84 of the cooler cover 80 in order to open and close the opening 84. A detailed configuration of the opening/closing member 90 will be described further below.

(2-7-2) Cooler

The cooler 70 is a cooling device that uses a vapor compression refrigeration cycle.

The cooler 70 has a first heat exchanger 72 that functions as a condenser, and a second heat exchanger 74 that functions as an evaporator (see FIGS. 6A and 6B). The first heat exchanger 72 and the second heat exchanger 74 are, e.g., fin-and-tube heat exchangers, but the type of heat exchanger is not limited to the fin-and-tube type. The type of heat exchanger to be used as the first heat exchanger 72 and the second heat exchanger 74 can be selected, as appropriate, from among various types of heat exchangers used for exchanging heat between air and a refrigerant. The cooler 70 is provided with a compressor (not shown) for compressing a gas refrigerant, and an expansion mechanism for causing high-pressure refrigerant to expand. The compressor, the first heat exchanger 72, the second heat exchanger 74, and the expansion mechanism are connected by a refrigerant tube to constitute a refrigerant circuit.

The cooler 70 has a first fan 76 and a second fan 78 (see FIGS. 6A and 6B). The first fan 76 takes in air from the opening 82 of the cooler cover 80 to supply air to the first heat exchanger 72, and air that has passed through the first heat exchanger 72 is expelled from the opening 84 of the cooler cover 80 to the exterior of the cooler cover 80. The second fan 78 takes in air from the first space B of the shield box 10 to supply air to the second heat exchanger 74, and air that has passed through the second heat exchanger 74 is blown out to the first space B of the shield box 10. In the present embodiment, the first fan 76 is a centrifugal blower, and the second fan 78 is an axial flow blower. However, the types of the first fan 76 and the second fan 78 are not limited to the exemplified types, and can be selected, as appropriate.

The cooler 70 functions roughly in the following manner.

The compressor compresses a low-temperature, low-pressure gas refrigerant to produce a high-temperature, high-pressure gas refrigerant. The refrigerant compressed by the compressor flows to the first heat exchanger 72 via the refrigerant tube. In the first heat exchanger 72, heat is exchanged between the refrigerant and the air in the space in which the X-ray inspection device 100 is installed. Specifically, in the first heat exchanger 72, the first fan 76 is operated to thereby exchange heat between the refrigerant and the air taken in from the opening 82 of the cooler cover 80, whereby the refrigerant releases heat and condenses, and meanwhile the air is heated. The heated air is exhausted from the opening 84 of the cooler cover 80 to the exterior of the cooler cover 80. In the first heat exchanger 72, refrigerant, which has released heat and condensed, becomes a low-temperature, high-pressure liquid refrigerant. The low-temperature, high-pressure liquid refrigerant that has passed through the first heat exchanger 72 flows to the expansion mechanism via the refrigerant tube. The expansion mechanism causes the low-temperature, high-pressure liquid refrigerant to decompress and expand to thereby convert the low-temperature, high-pressure liquid refrigerant into a gas-liquid two-phase refrigerant which is at low temperature and low pressure. The refrigerant decompressed/expanded by the expansion mechanism flows to the second heat exchanger 74 via the refrigerant tube. In the second heat exchanger 74, heat is exchanged between the refrigerant and the air in the first space B of the shield box 10, whereby the air inside the shield box 10 is cooled. Specifically, the second fan 78 is operated to thereby exchange heat, in the second heat exchanger 74, between the refrigerant and the air taken in from the first space B of the shield box 10, whereby the refrigerant evaporates, and meanwhile the air is cooled. The cooled air is blown into the first space B of the shield box 10. The low-temperature, low-pressure gas refrigerant that has passed through the second heat exchanger 74 flows again to the compressor via the refrigerant tube. Such a cycle is carried out in the refrigerant circuit of the cooler 70, whereby the cooler 70 cools the X-ray emitter 20 and other equipment disposed in the first space B of the shield box 10. A cooling device that uses a vapor compression refrigeration cycle is generally well known, and therefore, a further detailed description thereof is omitted.

The arrangement of the first heat exchanger 72, the second heat exchanger 74, the first fan 76, and the second fan 78 in the cooler 70 will be described with reference to FIGS. 6A and 6B.

The first heat exchanger 72, the second heat exchanger 74, the first fan 76, and the second fan 78 are disposed in the internal space A of the cooler cover 80.

The first heat exchanger 72 and the first fan 76 are disposed in the first internal space A1 (see FIGS. 6A and 6B). The first internal space A1 is in communication with the exterior of the cooler cover 80 via the openings 82, 84. The arrangement is not limited, but the first heat exchanger 72 is disposed on the upstream side of the first fan 76 in the direction of airflow generated by the first fan 76. When the first fan 76 is operated, air is taken in from the opening 82, and the air passes through the first heat exchanger 72 and is expelled from the opening 84 to the exterior of the cooler cover 80.

The second heat exchanger 74 and the second fan 78 are disposed in the second internal space A2 (see FIGS. 6A and 6B). The second internal space A2 is in communication with the first space B of the shield box 10 via the intake port 87 and the blow-out port 88, as shown in FIG. 6B. The arrangement is not limited, but the second heat exchanger 74 is disposed on the downstream side of the second fan 78 in the direction of airflow generated by the second fan 78. The second fan 78 takes in air of the first space B of the shield box 10 from the intake port 87 to supply air to the second heat exchanger 74, and the air that has passed through the second heat exchanger 74 is blown out from the blow-out port 88 to the first space B in the shield box 10.

In the present embodiment, the first internal space A1 is disposed in the rear portion of the internal space A, and the second internal space A2 is disposed in the forward area of the first internal space A1. However, the arrangement of the first internal space A1 and the second internal space A2 is not limited to the arrangement of the present embodiment as long as the above-described exchange of air is possible between the first internal space A1 and space outside the X-ray inspection device 100, and between the second internal space A2 and the first space B of the shield box 10.

(2-8) Opening/Closing Member

The opening/closing member 90 opens and closes the openings 82, 84 formed in the cooler cover 80. The opening/closing member 90 mainly includes a first door 92, a second door 94, a first securing mechanism 92a, and a second securing mechanism 94a (see FIGS. 9A and 9B).

The first door 92 opens and closes the opening 82. The second door 94 opens and closes the opening 84. In the present embodiment, the first door 92 and the second door 94 are manually operated doors. In the present embodiment, the first door 92 and the second door 94 are sliding doors that slide in the vertical direction along vertically extending tracks (not shown) that are fixed to an interior surface of the cooler cover 80. However, the structure and type of the first door 92 and the second door 94 are merely examples. For example, the first door 92 and the second door 94 may be sliding doors that slide in the lateral direction along horizontally extending tracks (not shown). The first door 92 and the second door 94 are both single-panel doors, but may also double-panel doors. The first door 92 and the second door 94 are not required to be sliding doors, and may be hinged doors that rotate about a hinge.

The first securing mechanism 92a secures the first door 92 in an open state, and keeps the first door 92 in an open state. The second securing mechanism 94a secures the second door 94 in an open state, and keeps the second door 94 in an open state. The first securing mechanism 92a and the second securing mechanism 94a mainly have a held part provided to the doors 92, 94, and a holding mechanism that is provided to the cooler cover 80 and holds the held part using elastic force and/or magnetic force. The first securing mechanism 92a and the second securing mechanism 94a may have a held part provided to the cooler cover 80, and a holding mechanism provided to the doors 92, 94. For example, a snap lock is used as the first securing mechanism 92a and the second securing mechanism 94a. Various mechanisms used for holding the position of a door can be selected, as appropriate, as the first securing mechanism 92a and the second securing mechanism 94a.

In the present embodiment, the opening/closing member 90 has only the securing mechanisms 92a, 94a for securing the doors 92, 94 in an open state, but no limitation is imposed thereby. In addition to the securing mechanisms 92a, 94a, the opening/closing member 90 may have a securing mechanism for securing the doors 92, 94 in a closed state.

When a closing force that spontaneously closes the opened doors 92, 94 does not act on the opened doors 92, 94, the opening/closing member 90 is not required to have the securing mechanisms 92a, 94a. However, the securing mechanisms 92a, 94a are preferably provided even when a spontaneous closing force does not act on the open doors 92, 94, in order to prevent the incidence such that the doors 92, 94 are closed unintentionally when the operator unintentionally bumps into the doors 92, 94.

(2-9) Resistance Mechanism

A resistance mechanism 200 is described below with reference to FIG. 7.

The resistance mechanism 200 is provided to both the first door 92 and the second door 94. The resistance mechanism 200 inhibits actuation that opens the first door 92, which has closed the opening 82 of the cooler cover 80. The resistance mechanism 200 also inhibits actuation that opens the second door 94, which has closed the opening 84 of the cooler cover 80.

The resistance mechanism 200 has a rack 220 provided to a frame 210 that extends in the sliding direction of the doors 92, 94. The resistance mechanism 200 also has a pinion gear 240 provided to a bracket 230 that extends from the doors 92, 94 to the frame 210 side in a direction orthogonal to the sliding direction of the doors 92, 94. The pinion gear 240 meshes with the rack 220 when the doors 92, 94 open and close. The resistance mechanism 200 has a brake mechanism 260 that is coupled to a rotating shaft 250 of the pinion gear 240 and that imparts a braking force (rotation resistance) to the rotating shaft 250. The type of brake mechanism 260 can be established, as appropriate. For example, a hydraulic brake mechanism that uses a trochoid pump is used. In the resistance mechanism 200, the rack 220 is disposed so that the pinion gear 240 provided to the bracket 230 of the doors 92, 94 is in a meshing state with the rack 220 in a state in which the doors 92, 94 have closed the openings 82, 84. By having the rack 220 disposed in such a position, it is possible for the resistance mechanism 200 to inhibit actuation that opens the doors 92, 94, which have closed the openings 82, 84. The brake mechanism 260 is preferably designed so that the doors 92, 94, which have closed the openings 82, 84, maintain the closed state of the openings 82, 84 against water discharge equivalent to IP69K.

The resistance mechanism 200 imparts a braking force to the rotating shaft 250 via the brake mechanism 260 also when the doors 92, 94 close, whereby movement speed of the doors 92, 94 can be slowed to reduce the possibility of the doors 92, 94 being vigorously shut and injuring the finger and/or hand of an operator.

However, providing a one-way clutch between the rotating shaft 250 and the brake mechanism 260 allows a configuration in which the braking force of the brake mechanism 260 is not transmitted to the rotating shaft 250 when the doors 92, 94 is closing. In the case of such a configuration, the X-ray inspection device 100 may have a resistance mechanism that inhibits actuation that closes the doors 92, 94 (slows the speed at which the doors 92, 94 close), separately from the resistance mechanism 200 that inhibits actuation that opens the doors 92, 94. Providing a resistance mechanism for actuation that opens and a separate resistance mechanism actuation that closes the doors 92, 94 makes it possible to impart a desirable braking force to both the actuation that opens and actuation that closes the doors 92, 94.

The resistance mechanism 200 described herein is merely an example. Various mechanisms that apply force in a direction that obstructs opening of the first door 92 and the second door 94 can be used as the resistance mechanism 200.

(2-10) Open/Close Sensor

An open/close sensor 96 senses opening/closing of the openings 82, 84 of the cooler cover 80 with the opening/closing member 90. The open/close sensor 96 is communicably connected to the controller 60 and transmits sensing results to the controller 60.

The open/close sensor 96 includes a sensor configured and disposed to sense the opening and closing of the opening 82 of the cooler cover 80 with the first door 92, and/or a sensor configured and disposed to sense the opening and closing of the opening 84 of the cooler cover 80 with the second door 94. The open/close sensor 96 preferably includes both a sensor configured and disposed to sense the opening and closing of the opening 82 of the cooler cover 80 with the first door 92, and a sensor configured and disposed to sense the opening and closing of the opening 84 of the cooler cover 80 with the second door 94.

The open/close sensor 96 may sense a state in which the doors 92, 94 have closed the openings 82, 84, and may sense a state in which the doors 92, 94 have not closed the openings 82, 84 (in other words, a state in which the doors 92, 94 are open).

For example, a photoelectric sensor that senses the presence of a detection target using a projector and a light receiver is used as the open/close sensor 96. A proximity sensor that senses, in a non-contact manner, a magnet mounted on the doors 92, 94 may also be used as the open/close sensor 96. Other types of sensors that can sense a state in which the doors 92, 94 are closed or opened may be provided to the open/close sensor 96.

The open/close sensor 96 is not required to be mounted on the cooler cover 80 and/or the doors 92, 94. For example, the open/close sensor 96 may sense opening/closing of the doors 92, 94 on the basis of an image of the X-ray inspection device 100 captured by a camera.

(2-11) Electronic Controller

The electronic controller 60 (also referred to herein as the controller 60) controls actuation of various pieces of equipment of the X-ray inspection device 100. The controller 60 generates an X-ray image on the basis of the amount of X-rays that have passed through the article P detected by the X-ray line sensor 30 during operation of the X-ray inspection device 100. The controller 60 inspects the quality of the article P on the basis of the generated X-ray image. In the present embodiment, the controller 60 inspects for foreign matter in the article P on the basis of the generated X-ray image.

The controller 60 is electrically connected to the X-ray emitter 20, the X-ray line sensor 30, the motor 44, the cooler 70, the open/close sensor 96, and the LCD monitor 50 (see FIG. 3). The controller 60 controls the operation of the various equipment 20, 30, 44, 70, 96, 50. The controller 60 receives various information from the X-ray line sensor 30, the open/close sensor 96, the LCD monitor 50, etc. The controller 60 is also communicably connected to the sorting device 4 that is disposed on the downstream side of the X-ray inspection device 100 and sorts, as defectives, articles P that have been determined to contain foreign matter by the X-ray inspection device 100.

The electronic controller 60 has a CPU 61 as an arithmetic and control device, and a storage device 65 that includes a ROM 62, a RAM 63, and a hard disk drive (HDD) 64, as shown in FIG. 3. The CPU 61, ROM 62, RAM 63, and HDD 64 are connected to each other via an address bus, a data bus, and other bus lines.

The controller 60 has a display control circuit, a key input circuit, and a communication port (none of which are shown). The display control circuit controls the display of data on the LCD monitor 50. The key input circuit takes in key-input data inputted using the touch panel function of the LCD monitor 50. The communication port enables connection of the controller 60 to a printer and other external equipment, and/or to a LAN or other network.

The storage device 65 stores various programs to be executed by the CPU 61, parameters used for inspecting for foreign matter in the article P, settings of the X-ray inspection device 100, and/or inspection results of the inspection for foreign matter. The parameters used in the inspection for foreign matter in the article P are, e.g., threshold values which is the amount of transmission X-rays used for assessing foreign matter. An example of a setting of the X-ray inspection device 100 is the speed for inspecting the article P.

The CPU 61 executes a program stored in the storage device 65, and thereby functions as an X-ray image generation unit 61a, a foreign matter presence inspection unit 61b, a notification unit 61c, and an operation-prohibiting unit 61d.

(2-11-1) X-Ray Image Generation Unit

The X-ray image generation unit 61a generates an X-ray image (transmission image) on the basis of the amount of transmission X-rays (amount of X-rays transmitted through the article P) detected by the X-ray line sensor 30. Specifically, the X-ray image generation unit 61a acquires, at short time intervals, data (X-ray transmission signals) related to the intensity of the transmission X-rays, the data being outputted by the X-ray detection elements 32 of the X-ray line sensor 30, and joins the data together chronologically in the form of a matrix to generate a transmission image of the article P.

(2-11-2) Foreign Matter Presence Inspection Unit

The foreign matter presence inspection unit 61*b* determines the presence of foreign matter contamination in the article P, on the basis of the X-ray image of the article P generated by the X-ray image generation unit 61*a*. The foreign matter presence inspection unit 61*b* has a number of determination methods. For example, the foreign matter presence inspection unit 61*b* sets a reference level (threshold value), and determines that foreign matter is contaminating the article P when a location darker than the reference level exists in the X-ray image generated by the X-ray image generation unit 61*a*. As a result of the determination by each determination method, the foreign matter presence inspection unit 61*b* determines that foreign matter is contaminating the article P if it is determined by any method that foreign matter is contaminating the article P. The result of the inspection for foreign matter is transmitted to the sorting device 4 disposed downstream from the X-ray inspection device 100. When it has been determined that there is foreign matter contamination, the controller 60 displays the fact of a defective product on the LCD monitor 50.

(2-11-3) Notification Unit

The CPU 61 preferably functions as the notification unit 61*c* that actuates in the following manner.

The notification unit 61*c* provides, on the basis of the sensing result produced by the open/close sensor 96, notification of information related to opening/closing (open/close-related information) of the openings 82, 84 of the cooler cover 80 with the opening/closing member 90. Specifically, the notification unit 61*c* provides, on the basis of sensing result produced by the open/close sensor 96, notification of open/close-related information by causing the open/close-related information to be displayed on the LCD monitor 50.

The notification unit 61*c* preferably issues notification of open/close-related information prior to or at the time of the start of operation of the X-ray inspection device 100. For example, when the open/close sensor 96 has sensed that the first door 92 and/or the second door 94 is closed, the notification unit 61*c* displays on the LCD monitor 50, as the open/close-related information prior to the start of operation of the X-ray inspection device 100 (e.g., 10 minutes before an operation start time stored in the storage device 65), a warning screen indicating that the first door 92 and/or second door 94 is closed, and/or a request screen for requesting that the first door 92 and/or the second door 94 be opened. In another example, when the open/close sensor 96 has sensed that the first door 92 and/or the second door 94 is closed at the start of operation of the X-ray inspection device 100 (e.g., when the operation start switch of the X-ray inspection device 100 has been pressed), the notification unit 61*c* displays on the LCD monitor 50, as the open/close-related information, a warning screen indicating that the first door 92 and/or second door 94 is closed, and/or a request screen for requesting that the first door 92 and/or the second door 94 be opened. In another example, when the open/close sensor 96 has sensed that the first door 92 and/or the second door 94 is closed prior to or at the start of operation of the X-ray inspection device 100, the notification unit 61*c* may display on the LCD monitor 50, as the open/close-related information, an indication that the X-ray inspection device 100 is inoperable, in addition to the above-noted open/close-related information or in lieu of the above-noted open/close-related information.

The notification unit 61*c* preferably issues notification of open/close-related information at the end of or after the end of operation of the X-ray inspection device 100. For example, at the end of operation of the X-ray inspection device 100 (e.g., when the operation stop switch of the X-ray inspection device 100 has been pressed) the notification unit 61*c* displays on the LCD monitor 50, as open/close-related information, a warning screen indicating that the first door 92 and/or second door 94 is open and/or a request screen for requesting that the first door 92 and/or the second door 94 be closed. In another example, when the open/close sensor 96 has sensed that the first door 92 and/or the second door 94 is open after the end of operation of the X-ray inspection device 100 (e.g., after the operation of the X-ray inspection device 100 has stopped), the notification unit 61*c* displays on the LCD monitor 50, as the open/close-related information, a warning screen indicating that the first door 92 and/or second door 94 is open, and/or a request screen for requesting that the first door 92 and/or the second door 94 be closed.

The notification unit 61*c* issues notification of open/close-related information by constantly displaying on the LCD monitor 50 whether the openings 82, 84 of the cooler cover 80 are opened or closed with the opening/closing member 90 on the basis of the detection result produced by the open/close sensor 96.

The mode of notification issued by the notification unit 61*c* is not limited to display on the LCD monitor 50. For example, the notification unit 61*c* may provide notification about open/close-related information by turning on a light. The notification unit 61*c* may also provide notification about open/close-related information by audio from a speaker. The notification unit 61*c* may also provide notification about open/close-related information by transmitting the open/close-related information to a computer (not shown) that remotely monitors the X-ray inspection device 100 and/or to a mobile terminal (not shown) carried by an operator.

(2-11-4) Operation-Prohibiting Unit

The CPU 61 preferably functions as the operation-prohibiting unit 61*d* that actuates in the following manner.

The operation-prohibiting unit 61*d* prohibits operation of the X-ray inspection device 100 when the open/close sensor 96 has sensed that the openings 82, 84 of the cooler cover 80 have been closed with the opening/closing member 90.

For example, when the open/close sensor 96 has sensed that the opening 82 and/or the opening 84 of the cooler cover 80 is closed with the first door 92 and/or the second door 94, the operation-prohibiting unit 61*d* preferably prohibits operation of the X-ray inspection device 100 even when the stopped X-ray inspection device 100 has been instructed to start operation.

In another example, the operation-prohibiting unit 61*d* preferably prohibits operation of the X-ray inspection device 100 (stops operation of the X-ray inspection device 100) when the open/close sensor 96 has sensed during operation of the X-ray inspection device 100 that the opening 82 and/or the opening 84 of the cooler cover 80 are closed with the first door 92 and/or the second door 94.

The notification unit 61*c* preferably issues notification that the X-ray inspection device 100 is inoperable when the operation-prohibiting unit 61*d* is prohibiting operation of the X-ray inspection device 100 and/or when the operation-prohibiting unit 61*d* has stopped the X-ray inspection device 100 during operation.

(3) Characteristics (3-1)

The X-ray inspection device 100 of the present embodiment is provided with the X-ray emitter 20 as an example of an X-ray source, the cooler 70, the cooler cover 80, and the opening/closing member 90. The cooler 70 cools the X-ray emitter 20. The cooler cover 80 covers the cooler 70. The cooler cover 80 has the openings 82, 84 formed therein via which the interior and exterior communication. The opening/closing member 90 opens and closes the openings 82, 84 formed in the cooler cover 80.

In the present embodiment, the opening/closing member 90 has the first door 92 that opens and closes the opening 82 formed in the cooler cover 80, and the second door 94 that opens and closes the opening 84 formed in the cooler cover 80.

In the X-ray inspection device 100 according to the present embodiment, the opening/closing member 90 for opening and closing the openings 82, 84 of the cooler cover 80 is provided to the openings of the cooler cover that is used to take in external air and supply the air to the cooler 70 and to exhaust the air heated by the cooler 70 to the exterior. Consequently, in the present X-ray inspection device 100, the possibility of water flowing into the cooler cover 80 during a washing operation can be reduced. A cleaning operator can perform cleaning operation without paying close attention to the inflow of water from the openings 82, 84 of the cooler cover 80, and cleaning time can therefore be reduced.

(3-2)

The X-ray inspection device 100 of the present embodiment is provided with the open/close sensor 96. The open/close sensor 96 senses opening/closing of the openings 82, 84 of the cooler cover 80 with the opening/closing member 90.

Preferably, the open/close sensor 96 includes a sensor for sensing opening and closing of the opening 82 of the cooler cover 80 with the first door 92, and a sensor for sensing opening and closing of the opening 84 of the cooler cover 80 with the second door 94.

In the X-ray inspection device 100 of the present embodiment, opening and closing of the openings 82, 84 of the cooler cover 80 are sensed by the open/close sensor 96. Consequently, it is easy to monitor the occurrence of a mistake such as the openings 82, 84 of the cooler cover 80 being open when the openings should be closed, or conversely, the openings 82, 84 of the cooler cover 80 being closed when the openings should be open.

(3-3)

The X-ray inspection device 100 of the present embodiment is provided with a notification unit 61c. The notification unit 61c provides, on the basis of the sensing result produced by the open/close sensor 96, notification of information related to opening or closing of the openings 82, 84 of the cooler cover 80 by the opening/closing member 90.

In the present X-ray inspection device 100, information related to the opening and closing of the openings 82, 84 of the cooler cover 80 is provided. Consequently, it is easy to suppress the occurrence of a mistake such as the openings 82, 84 of the cooler cover 80 being open when the openings should be closed, or conversely, the openings 82, 84 being closed when the openings should be open.

(3-4)

In the X-ray inspection device 100 of the present embodiment, the notification unit 61c issues notification of information related to opening and closing of the openings 82, 84 of the cooler cover 80 with the opening/closing member 90, prior to the start of operation or at the time of the start of operation of the X-ray inspection device 100.

In the present X-ray inspection device 100, it is easy to suppress the incidence of situations in which the X-ray inspection device 100 is operated with the openings 82, 84 of the cooler cover 80 closed even though the X-ray emitter 20 needs to be cooled.

(3-5)

In the X-ray inspection device 100 of the present embodiment, the notification unit 61c issues notification of information related to opening and closing of the openings 82, 84 of the cooler cover 80 with the opening/closing member 90, at the end of operation or after the end of operation of the X-ray inspection device 100.

In the present X-ray inspection device 100, notification of information related to opening/closing of the openings 82, 84 of the cooler cover 80 with the opening/closing member 90 is provided at the end of operation of the X-ray inspection device 100 or after the end of operation of the X-ray inspection device 100 when there is a possibility that the X-ray inspection device 100 will be washed thereafter. Accordingly, in the present X-ray inspection device 100, it is easy to suppress the incidence of situations in which the X-ray inspection device 100 is washed with the openings 82, 84 of the cooler cover 80 left open.

(3-6)

In the X-ray inspection device 100 of the present embodiment, the notification unit 61c issues notification that the X-ray inspection device 100 is inoperable when the open/close sensor 96 senses that the openings 82, 84 of the cooler cover 80 is closed with the opening/closing member 90.

In the present X-ray inspection device 100, it is easy to suppress the incidence of situations in which the X-ray inspection device 100 is operated with the openings 82, 84 of the cooler cover 80 closed even though the X-ray emitter 20 needs to be cooled.

(3-7)

The X-ray inspection device 100 of the present embodiment is provided with an operation-prohibiting unit 61d. The operation-prohibiting unit 61d prohibits operation of the X-ray inspection device 100 when the open/close sensor 96 senses that the openings 82, 84 of the cooler cover 80 are closed with the opening/closing member 90.

In the present X-ray inspection device 100, the X-ray inspection device 100 cannot be operated with the openings 82, 84 of the cooler cover 80 closed, and it is therefore possible to suppress the incidence of problems such as overheating of the X-ray emitter 20 and other components.

(3-8)

In the present X-ray inspection device 100, the cooler cover 80 defines a rectangular parallelepiped internal space A.

In the present X-ray inspection device 100, the cooler cover 80 can be realized with a simple shape.

(3-9)

The present X-ray inspection device 100 is provided with a resistance mechanism 200. The resistance mechanism 200 inhibits opening actuation of the opening/closing member 90, which is closing the openings 82, 84 of the cooler cover 80. The resistance mechanism 200, which inhibits opening actuation of the doors 92, 94, is preferably provided to the first door 92, which closes the opening 82 of the cooler cover 80, and the second door 94, which closes the opening 84 of the cooler cover 80.

In the present X-ray inspection device 100, opening actuation of the opening/closing member 90 is inhibited by the presence of the resistance mechanism 200. Consequently, the configuration is highly convenient in that it is possible to suppress the opening/closing member 90 from readily opening and water flowing into the interior during washing of the X-ray inspection device 100, even if the opening/closing member 90 is not secured by some means.

(3-10)

In the present X-ray inspection device 100, the resistance mechanism 200 maintains, against water discharge equivalent to IP69K, a state in which the openings 82, 84 of the cooler cover 80 is closed with the opening/closing member 90, which closes the openings 82, 84.

In present X-ray inspection device 100, the state in which the openings 82, 84 of the cooler cover 80 are closed with the opening/closing member 90 is maintained even when water discharge equivalent to IP69K is performed. Consequently, even when high-pressure washing of the X-ray inspection device 100 is performed for the purpose of disinfection or sterilization, it is possible to suppress the opening/closing member 90 from readily opening and water flowing into the interior during washing of the X-ray inspection device 100.

(4) Modifications

Modifications of the foregoing embodiment are described below. Modifications may be combined, as appropriate, as long as there is no mutual contradiction.

(4-1) Modification A

In the embodiment above, two openings 82, 84 are formed in the cooler cover 80, but the number of openings formed in the cooler cover 80 is not limited to two. For example, a single opening formed in the cooler cover 80 may achieve the functions of both an intake port and an exhaust port. Three or more openings may be formed in the cooler cover 80.

(4-2) Modification B

In the embodiment above, the opening/closing member 90 has doors 92, 94 that open and close the openings 82, 84 of the cooler cover 80, but no limitation is imposed thereby. For example, in lieu of the doors 92, 94, the opening/closing member 90 may have a shutter that opens and closes the openings 82, 84 of the cooler cover 80.

(4-3) Modification C

The cooler cover 80 of the above-described embodiment defines a rectangular parallelepiped internal space A. However, no limitation is imposed thereby.

Figure 10A:
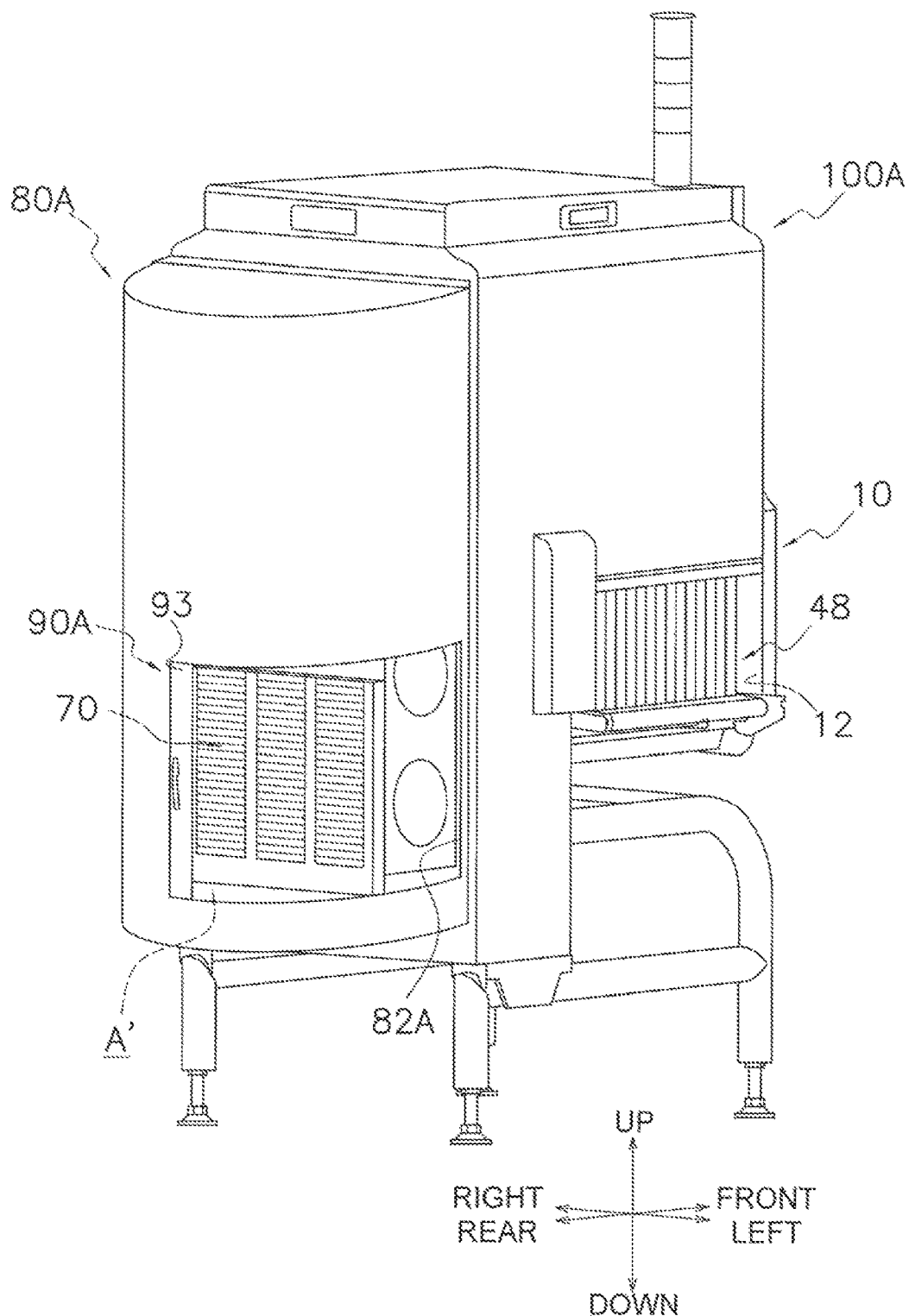
FIG. 10A is a simplified perspective view as seen diagonally from the rear of the X-ray inspection device of modification C, and depicts a state in which the opening/closing member provided to the openings of the cooler cover is open.
Figure 10B:
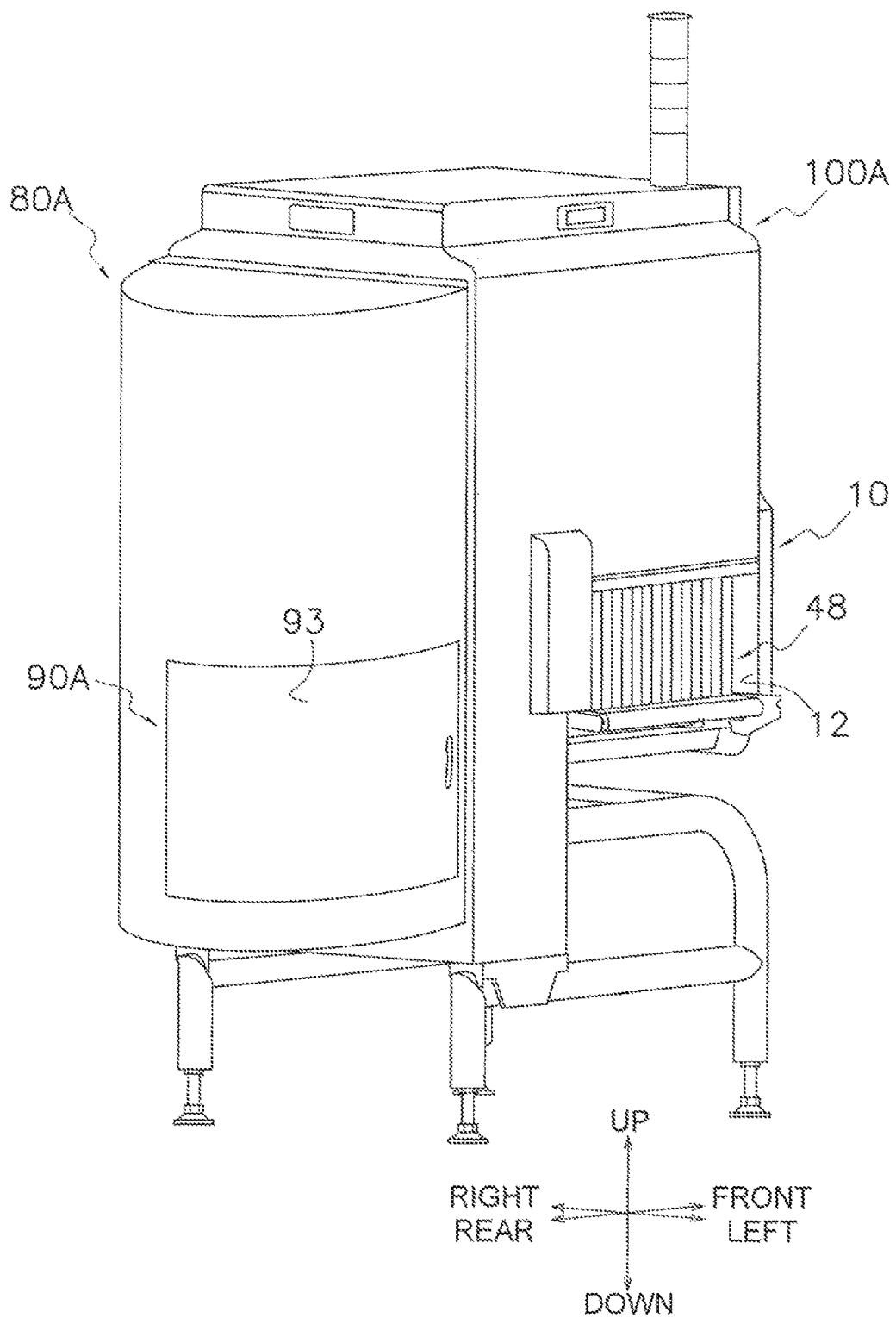
FIG. 10B is a simplified perspective view as seen diagonally from the rear of the X-ray inspection device of modification C, and depicts a state in which the opening/closing member provided to the openings of the cooler cover is closed.

For example, an X-ray inspection device 100A may have a cooler cover 80A that defines a semi-cylindrical internal space A', as shown in FIGS. 10A and 10B. The semi-cylindrical shape herein is not limited to a shape obtained by dividing a regular cylinder into right halves along a plane parallel to the axial direction of the cylinder passing through the center of a perfect circle. The semi-cylindrical shape herein includes a shape obtained by dividing a regular cylinder into substantial halves along a plane parallel to or substantially parallel to the axial direction of the cylinder. The semi-cylindrical shape herein includes a shape obtained by dividing an ellipsoidal cylinder into right halves or substantial halves along a plane parallel to or substantially parallel to the axial direction of the ellipsoidal cylinder.

Rather than two openings 82, 84, a single opening 82A is formed in the cooler cover 80A of the X-ray inspection device 100A. The opening 82A doubles in function of both an intake port and an exhaust port. An opening/closing member 90A of the X-ray inspection device 100A has a single door 93. In the X-ray inspection device 100A, there is a single opening 82A of the cooler cover 80A, and therefore, the opening 82A can open and close using a single door 93, and failing to open and/or close the door 93 is particularly easy to suppress.

Except for the external shape appearance of the cooler cover 80A and the configuration of the opening/closing member 90A, the X-ray inspection device 100A is the same as the X-ray inspection device 100 of the above-described embodiment, and a description is otherwise omitted.

(4-4) Modification D

In the embodiment above, the first door 92 and the second door 94 of the opening/closing member 90 are manually opened and closed, but no limitation is imposed thereby.

The first door 92 and the second door 94 of the opening/closing member 90 may open and close using a motor, air pressure, or hydraulic or other force. The first door 92 and the second door 94 of the opening/closing member 90 may open and close by manipulation of a switch by an operation staff, and may automatically open and close by instruction of the controller 60. When the first door 92 and the second door 94 of the opening/closing member 90 open and close automatically, the controller 60, e.g., opens the doors 92, 94 at the start of operation of the X-ray inspection device 100, and closes the doors 92, 94 at the end of operation of the X-ray inspection device 100.

(4-5) Modification E

In the embodiment above, the electronic controller 60 functions as the operation-prohibiting unit 61d. However, the operation-prohibiting unit 61d may be separate from the electric controller 60.

For example, the operation-prohibiting unit may include an electric circuit with relay switch. Such an operation-prohibiting unit may prohibit the operation of the components of the X-ray inspection device 100 with a configuration that the relay contact is not turned on when the when the open/close sensor 96 senses that the opening/closing member 90 are in the closed orientation.

INDUSTRIAL APPLICABILITY

The present invention can be widely used in X-ray inspection devices.

What is claimed:

1. An X-ray inspection device comprising:
an X-ray source;
a cooler configured to cool the X-ray source;
a cooler cover covering the cooler, the cooler cover having an opening formed therein that extends between an interior of the cooler cover and an exterior of the cooler cover;
an opening/closing member movable between an open orientation opening the opening and a closed orientation closing the opening; and
a conveyor mechanism configured to receive an article conveyed into the X-ray inspection device, convey the article so as to pass through an inspection space, and deliver the article to a downstream side of the X-ray inspection device.

2. The X-ray inspection device according to claim 1, further comprising an open/close sensor that senses the orientation of the opening/closing member.

3. The X-ray inspection device according to claim 2, further comprising an electronic controller that includes a notification unit that issues notification of information related to opening/closing of the opening with the opening/closing member in response to signals from the open/close sensor.

4. The X-ray inspection device according to claim 3, wherein, at least prior to a start of operation of the X-ray inspection device or at the time of the start of operation of the X-ray inspection device, the notification unit of the electronic controller issues notification of information related to the orientation of the opening/closing member.

5. The X-ray inspection device according to claim 3, wherein, at least at an end of operation of the X-ray inspection device or after the end of operation of the X-ray inspection device, the notification unit of the electronic controller issues notification of information related to the orientation of the opening/closing member.

6. The X-ray inspection device according claim 3, wherein the notification unit of the electronic controller issues notification that the X-ray inspection device is inoperable when the open/close sensor senses that the opening/closing member is in the closed orientation.

7. The X-ray inspection device according to claim 2, further comprising an operation-prohibiting unit that prohibits operation of the X-ray inspection device when the open/close sensor senses that the opening/closing member is in the closed orientation.

8. The X-ray inspection device according to claim 1, wherein the cooler cover defines one of a rectangular parallelepiped or semi-cylindrical space.

9. The X-ray inspection device according to claim 1, further comprising a resistance mechanism that inhibits opening actuation of the opening/closing member with the opening/closing member in the closed orientation.

10. The X-ray inspection device according to claim 9, wherein the resistance mechanism maintains, against water discharge equivalent to IP69K, a state in which the opening/closing member is in the closed orientation.

* * * * *